US012484911B2

(12) United States Patent
Hopkinson et al.

(10) Patent No.: US 12,484,911 B2
(45) Date of Patent: Dec. 2, 2025

(54) INFLATABLE RADIAL ARTERY COMPRESSION DEVICE WITH CINCHING WRISTBAND AND METHOD OF USE

(71) Applicant: Merit Medical Systems, Inc., South Jordan, UT (US)

(72) Inventors: Aaron Hopkinson, Herriman, UT (US); Jacquelyn Monroe, Highland, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 23 days.

(21) Appl. No.: 17/399,827

(22) Filed: Aug. 11, 2021

(65) Prior Publication Data

US 2022/0047272 A1 Feb. 17, 2022

Related U.S. Application Data

(60) Provisional application No. 63/065,318, filed on Aug. 13, 2020.

(51) Int. Cl.
*A61B 17/132* (2006.01)
*A61B 17/135* (2006.01)

(52) U.S. Cl.
CPC ........ *A61B 17/1322* (2013.01); *A61B 17/135* (2013.01)

(58) Field of Classification Search
CPC .............. A61B 17/1322; A61B 17/135; A61B 17/1355; A61B 17/132
See application file for complete search history.

(56) References Cited

U.S. PATENT DOCUMENTS

| | | | |
|---|---|---|---|
| 2,547 | A | 4/1842 | Welchman |
| 11,623 | A | 8/1854 | Waters |
| 44,843 | A | 10/1864 | Smith |
| 1,177,208 | A | 3/1916 | Pierpont |
| 1,197,232 | A | 9/1916 | Pierpont |
| 1,281,653 | A | 10/1918 | Plummer |
| 2,332,107 | A | 10/1943 | Nieburgs |
| 2,397,257 | A | 3/1946 | Goland et al. |
| 3,003,500 | A | 10/1961 | Barton et al. |
| 3,021,841 | A | 2/1962 | Burke |
| 3,050,064 | A | 8/1962 | Moore et al. |
| 3,058,627 | A | 10/1962 | Eskridge |
| 3,115,138 | A | 12/1963 | Mcelvenny et al. |

(Continued)

FOREIGN PATENT DOCUMENTS

| | | |
|---|---|---|
| CA | 2546434 | 1/2013 |
| CN | 201205292 | 3/2009 |

(Continued)

OTHER PUBLICATIONS

Lodi, et al., A New Portable Chest Drainage Device, Ann, Thorac. Surg., vol. 69 ,2000 ,998-1001.

(Continued)

*Primary Examiner* — Katherine H Schwiker
(74) *Attorney, Agent, or Firm* — Dorsey & Whitney LLP

(57) ABSTRACT

Radial artery compression devices are disclosed. Some embodiments comprise an inflatable chamber and a frame. Securement straps, including securement straps comprising a free end threaded through a portion of the frame are also disclosed. Systems and methods for securing and/or positioning a securement device with one hand are also disclosed.

14 Claims, 18 Drawing Sheets

(56) References Cited

U.S. PATENT DOCUMENTS

| | | | |
|---|---|---|---|
| 3,233,610 | A | 2/1966 | Wade |
| 3,241,554 | A | 3/1966 | Coanda |
| 3,253,594 | A | 5/1966 | Matthews |
| 3,312,221 | A | 4/1967 | Overment |
| 3,315,802 | A | 4/1967 | Lonholdt et al. |
| 3,319,684 | A | 5/1967 | Calhoun |
| 3,340,869 | A | 9/1967 | Bane |
| 3,363,626 | A | 1/1968 | Bidwell et al. |
| 3,376,868 | A | 4/1968 | Mondiadis |
| 3,417,750 | A | 12/1968 | Carson |
| 3,419,010 | A | 12/1968 | Williamson |
| 3,459,189 | A | 8/1969 | Alley |
| 3,487,837 | A | 1/1970 | Petersen |
| 3,542,026 | A | 11/1970 | Bledsoe |
| 3,554,580 | A | 1/1971 | Goyke |
| 3,566,875 | A | 3/1971 | Stoehr |
| 3,572,340 | A | 3/1971 | Lloyd et al. |
| 3,650,507 | A | 3/1972 | Nyberg et al. |
| 3,680,562 | A | 8/1972 | Wittes et al. |
| 3,683,929 | A | 8/1972 | Holter |
| 3,742,952 | A | 7/1973 | Magers et al. |
| 3,752,158 | A | 8/1973 | Kariher |
| 3,768,476 | A | 10/1973 | Raitto |
| 3,774,611 | A | 11/1973 | Tussey et al. |
| 3,777,757 | A | 12/1973 | Gray et al. |
| 3,783,870 | A | 1/1974 | Schachet |
| 3,809,087 | A | 5/1974 | Lewis |
| 3,820,546 | A | 6/1974 | Chittenden et al. |
| 3,853,127 | A | 12/1974 | Spademan |
| 3,875,941 | A | 4/1975 | Adair |
| 3,920,023 | A | 11/1975 | Dye et al. |
| 3,960,153 | A | 6/1976 | Carey et al. |
| 3,982,546 | A | 9/1976 | Friend |
| 4,022,209 | A | 5/1977 | Nehring |
| 4,029,095 | A | 6/1977 | Pena |
| 4,073,294 | A | 2/1978 | Stanley et al. |
| 4,105,031 | A | 8/1978 | Kurtz et al. |
| 4,112,949 | A | 9/1978 | Rosenthal et al. |
| 4,116,366 | A | 9/1978 | Takenakashima et al. |
| 4,120,715 | A | 10/1978 | Ockwell et al. |
| 4,136,696 | A | 1/1979 | Nehring |
| 4,143,853 | A | 3/1979 | Abramson |
| 4,153,058 | A | 5/1979 | Nehme |
| 4,170,300 | A | 10/1979 | Pick |
| 4,174,053 | A | 11/1979 | Shimizu |
| 4,187,848 | A | 2/1980 | Taylor |
| 4,203,445 | A | 5/1980 | Jessup et al. |
| 4,214,593 | A | 7/1980 | Imbruce et al. |
| 4,257,629 | A | 3/1981 | Maple et al. |
| 4,265,848 | A | 5/1981 | Rusch et al. |
| 4,266,545 | A | 5/1981 | Moss |
| 4,310,104 | A | 1/1982 | Takatsuki |
| 4,315,513 | A | 2/1982 | Nawash et al. |
| 4,334,551 | A | 6/1982 | Pfister |
| 4,341,212 | A | 7/1982 | Medwid |
| D267,433 | S | 12/1982 | Pageau |
| 4,364,395 | A | 12/1982 | Redmond et al. |
| D267,815 | S | 2/1983 | Elliott et al. |
| 4,382,442 | A | 5/1983 | Jones |
| 4,390,519 | A | 6/1983 | Sawyer |
| 4,392,858 | A | 7/1983 | George et al. |
| 4,393,873 | A | 7/1983 | Nawash et al. |
| 4,396,382 | A | 8/1983 | Goldhaber |
| 4,402,682 | A | 9/1983 | Garver, Sr. et al. |
| 4,421,146 | A | 12/1983 | Bond et al. |
| 4,427,425 | A | 1/1984 | Briggs et al. |
| 4,429,693 | A | 2/1984 | Blake et al. |
| 4,433,973 | A | 2/1984 | Kurtz et al. |
| 4,439,190 | A | 3/1984 | Protzmann et al. |
| 4,447,235 | A | 5/1984 | Clarke |
| 4,455,141 | A | 6/1984 | Todd |
| 4,464,168 | A | 8/1984 | Redmond et al. |
| 4,475,904 | A | 10/1984 | Wang |
| 4,476,866 | A | 10/1984 | Chin |
| 4,479,495 | A | 10/1984 | Isaacson |
| 4,479,818 | A | 10/1984 | Briggs et al. |
| 4,490,003 | A | 12/1984 | Robinson |
| 4,496,464 | A | 1/1985 | Hensley |
| 4,501,363 | A | 2/1985 | Isbey, Jr. |
| 4,511,163 | A | 4/1985 | Harris et al. |
| 4,512,771 | A | 4/1985 | Norton |
| 4,525,167 | A | 6/1985 | Goldberg et al. |
| 4,539,985 | A | 9/1985 | Magrath |
| 4,543,100 | A | 9/1985 | Brodsky |
| 4,557,262 | A | 12/1985 | Snow |
| 4,564,222 | A | 1/1986 | Loker et al. |
| 4,569,674 | A | 2/1986 | Phillips et al. |
| 4,583,972 | A | 4/1986 | Hunter, III et al. |
| 4,605,400 | A | 8/1986 | Kurtz et al. |
| 4,610,469 | A | 9/1986 | Wolff-Mooij |
| 4,610,671 | A | 9/1986 | Luther |
| 4,620,846 | A | 11/1986 | Goldberg et al. |
| 4,642,088 | A | 2/1987 | Gunter |
| 4,643,720 | A | 2/1987 | Lanciano |
| 4,648,870 | A | 3/1987 | Goldberg et al. |
| 4,666,433 | A | 5/1987 | Parks |
| 4,669,463 | A | 6/1987 | McConnell |
| 4,673,398 | A | 6/1987 | Turner et al. |
| 4,675,020 | A | 6/1987 | Mcphee |
| 4,681,571 | A | 7/1987 | Nehring |
| 4,685,901 | A | 8/1987 | Parks |
| 4,685,908 | A | 8/1987 | Kurtz |
| 4,701,163 | A | 10/1987 | Parks |
| 4,702,733 | A | 10/1987 | Wright et al. |
| 4,706,830 | A | 11/1987 | Wareing |
| 4,738,671 | A | 4/1988 | Elliott et al. |
| 4,740,202 | A | 4/1988 | Stacey et al. |
| 4,741,678 | A | 5/1988 | Nehring |
| 4,747,843 | A | 5/1988 | Felix et al. |
| 4,747,844 | A | 5/1988 | Elliott |
| 4,752,292 | A | 6/1988 | Lopez et al. |
| 4,758,238 | A | 7/1988 | Sundblom et al. |
| 4,781,674 | A | 11/1988 | Redmond et al. |
| 4,790,567 | A | 12/1988 | Kawano et al. |
| 4,809,679 | A | 3/1989 | Shimonaka et al. |
| 4,813,929 | A | 3/1989 | Semrad |
| 4,820,288 | A | 4/1989 | Isono |
| 4,828,546 | A | 5/1989 | Mcneil et al. |
| 4,834,702 | A | 5/1989 | Rocco |
| 4,834,802 | A | 5/1989 | Prier |
| 4,844,087 | A | 7/1989 | Garg |
| 4,850,955 | A | 7/1989 | Newkirk |
| 4,857,042 | A | 8/1989 | Schneider |
| 4,863,593 | A | 9/1989 | Quick |
| 4,867,740 | A | 9/1989 | East |
| 4,874,377 | A | 10/1989 | Newgard et al. |
| 4,883,474 | A | 11/1989 | Sheridan et al. |
| 4,883,476 | A | 11/1989 | Kurtz et al. |
| 4,921,488 | A | 5/1990 | Maitz et al. |
| 4,928,830 | A | 5/1990 | Brewer |
| 4,929,235 | A | 5/1990 | Merry et al. |
| 4,930,997 | A | 6/1990 | Bennett |
| 4,936,837 | A | 6/1990 | Wexler |
| 4,944,732 | A | 7/1990 | Russo |
| 4,946,448 | A | 8/1990 | Richmond |
| 4,946,449 | A | 8/1990 | Davis, Jr. |
| 4,949,756 | A | 8/1990 | Melinyshyn et al. |
| 4,950,256 | A | 8/1990 | Luther et al. |
| 4,960,412 | A | 10/1990 | Fink |
| 4,966,197 | A | 10/1990 | Jaron et al. |
| 4,968,294 | A | 11/1990 | Salama |
| 4,969,879 | A | 11/1990 | Lichte |
| 4,969,890 | A | 11/1990 | Sugita et al. |
| 4,973,311 | A | 11/1990 | Iwakoshi et al. |
| 4,981,474 | A | 1/1991 | Bopp et al. |
| 4,995,864 | A | 2/1991 | Bartholomew et al. |
| 5,002,528 | A | 3/1991 | Palestrant |
| 5,002,529 | A | 3/1991 | Cunningham |
| 5,009,226 | A | 4/1991 | Holt |
| 5,009,635 | A | 4/1991 | Scarberry |
| 5,009,636 | A | 4/1991 | Wortley et al. |
| 5,019,059 | A | 5/1991 | Goldberg et al. |
| 5,019,096 | A | 5/1991 | Fox, Jr. et al. |
| 5,024,653 | A | 6/1991 | Kohnka |

(56) References Cited

U.S. PATENT DOCUMENTS 5,037,403 A 8/1991 Garcia
5,048,875 A 9/1991 Usui et al.
5,052,998 A 10/1991 Zimmon
5,053,014 A 10/1991 Van Heugten
5,057,084 A 10/1991 Ensminger et al.
5,060,833 A 10/1991 Edison et al.
5,061,255 A 10/1991 Greenfeld et al.
5,062,835 A 11/1991 Maitz et al.
5,064,416 A 11/1991 Newgard et al.
5,078,677 A 1/1992 Gentelia et al.
5,078,689 A 1/1992 Keller
5,078,699 A 1/1992 Haber et al.
5,085,349 A 2/1992 Fawcett
5,092,850 A 3/1992 Buma
5,098,405 A 3/1992 Peterson et al.
5,100,394 A 3/1992 Dudar et al.
5,102,404 A 4/1992 Goldberg et al.
5,106,054 A 4/1992 Mollenauer et al.
5,112,323 A 5/1992 Winkler et al.
5,123,677 A 6/1992 Kreczko et al.
5,137,524 A 8/1992 Lynn et al.
5,139,512 A 8/1992 Dreiling et al.
5,141,499 A 8/1992 Zappacosta
5,156,597 A 10/1992 Verreet et al.
5,165,953 A 11/1992 Shlenker et al.
5,188,622 A 2/1993 Muller et al.
5,199,946 A 4/1993 Abramowitz
5,207,655 A 5/1993 Sheridan
5,215,538 A 6/1993 Larkin
5,234,454 A 8/1993 Bangs
5,238,217 A 8/1993 Fell
5,242,422 A 9/1993 Schneberger et al.
5,251,873 A 10/1993 Atkinson et al.
5,261,897 A 11/1993 Kurtz et al.
5,269,771 A 12/1993 Thomas et al.
5,269,803 A 12/1993 Geary et al.
5,279,551 A 1/1994 James
5,279,601 A 1/1994 Lichte
5,280,876 A 1/1994 Atkins
5,295,657 A 3/1994 Atkinson
5,295,658 A 3/1994 Atkinson et al.
5,300,034 A 4/1994 Behnke et al.
5,300,048 A 4/1994 Drewes, Jr. et al.
5,304,121 A 4/1994 Sahatjian
5,304,186 A 4/1994 Semler et al.
5,304,201 A 4/1994 Rice
5,307,811 A 5/1994 Sigwart et al.
5,309,924 A 5/1994 Peabody
5,320,110 A 6/1994 Wang
5,322,518 A 6/1994 Schneider et al.
5,330,447 A 7/1994 Barth
5,334,159 A 8/1994 Turkel
5,334,166 A 8/1994 Palestrant
5,344,401 A 9/1994 Radisch et al.
5,345,929 A 9/1994 Jansson et al.
5,352,198 A 10/1994 Goldenberg et al.
5,356,391 A 10/1994 Stewart
5,360,413 A 11/1994 Leason et al.
5,390,898 A 2/1995 Smedley et al.
5,399,165 A 3/1995 Paul, Jr.
5,401,245 A 3/1995 Haining
5,403,284 A 4/1995 Gross
5,405,331 A 4/1995 Bahnke et al.
5,407,434 A 4/1995 Gross
5,423,334 A 6/1995 Jordan
5,435,470 A 7/1995 Kim
5,437,900 A 8/1995 Kuzowski
5,456,675 A 10/1995 Wolbring et al.
5,465,857 A 11/1995 Yang
5,470,319 A 11/1995 Mayer
5,472,325 A 12/1995 Svendsen
5,472,435 A 12/1995 Sutton
5,480,392 A 1/1996 Mous
5,484,401 A 1/1996 Rodriguez
5,489,269 A 2/1996 Aldrich et al.
5,492,304 A 2/1996 Smith et al.
5,494,043 A 2/1996 Osullivan et al.
5,496,299 A 3/1996 Felix et al.
5,501,426 A 3/1996 Atkinson et al.
5,505,717 A 4/1996 Moore
5,507,733 A 4/1996 Larkin
5,507,847 A 4/1996 George et al.
5,509,433 A 4/1996 Paradis
5,509,909 A 4/1996 Moy
5,509,912 A 4/1996 Vaillancourt et al.
5,512,056 A 4/1996 Stevens et al.
5,514,117 A 5/1996 Lynn
5,520,665 A 5/1996 Fleetwood et al.
5,529,278 A 6/1996 Weldon et al.
5,535,785 A 7/1996 Werge et al.
5,540,661 A 7/1996 Tomisaka et al.
5,556,387 A 9/1996 Mollenauer et al.
5,573,516 A 11/1996 Tyner
5,576,072 A 11/1996 Hostettler et al.
5,597,536 A 1/1997 Mayer
5,613,491 A 3/1997 Kanner et al.
5,628,735 A 5/1997 Skow
5,628,908 A 5/1997 Kamen et al.
5,636,875 A 6/1997 Wasser et al.
5,637,103 A 6/1997 Kerwin et al.
5,662,960 A 9/1997 Hostettler et al.
5,674,192 A 10/1997 Sahatjian et al.
5,676,346 A 10/1997 Leinsing
D385,889 S 11/1997 Kullas et al.
5,685,866 A 11/1997 Lopez
5,690,612 A 11/1997 Lopez et al.
5,695,466 A 12/1997 Lopez et al.
5,695,520 A 12/1997 Bruckner et al.
5,701,934 A 12/1997 Kuran et al.
5,709,672 A 1/1998 Illner
5,725,506 A 3/1998 Freeman et al.
5,727,714 A 3/1998 Fawcett
5,728,120 A 3/1998 Shani et al.
5,733,496 A 3/1998 Avellanet
5,735,826 A 4/1998 Richmond
5,738,144 A 4/1998 Rogers
5,738,656 A 4/1998 Wagner
5,776,119 A 7/1998 Bilbo et al.
5,779,657 A 7/1998 Daneshvar
5,792,098 A 8/1998 Felix et al.
5,792,108 A 8/1998 Felix et al.
5,807,348 A 9/1998 Zinger et al.
5,810,792 A 9/1998 Fangrow, Jr. et al.
5,814,024 A 9/1998 Thompson et al.
5,823,961 A 10/1998 Fields et al.
5,830,185 A 11/1998 Block, Jr.
5,839,715 A 11/1998 Leinsing
5,873,853 A 2/1999 Keilman et al.
5,897,782 A 4/1999 Chatelin et al.
5,904,334 A 5/1999 Grunert et al.
5,921,972 A 7/1999 Skow
5,937,885 A 8/1999 Sampson
5,938,176 A 8/1999 Falconer
5,944,703 A 8/1999 Dixon et al.
5,947,953 A 9/1999 Ash et al.
5,954,313 A 9/1999 Ryan
5,954,706 A 9/1999 Sahatjian
5,957,898 A 9/1999 Jepson et al.
5,957,912 A 9/1999 Heitzmann
5,961,497 A 10/1999 Larkin
5,971,357 A 10/1999 Denton et al.
5,972,441 A 10/1999 Campbell et al.
5,976,650 A 11/1999 Campbell et al.
5,984,891 A 11/1999 Keilman et al.
5,997,486 A 12/1999 Burek et al.
5,997,564 A 12/1999 Shehata et al.
6,001,079 A 12/1999 Pourchez
6,024,731 A 2/2000 Seddon et al.
6,025,044 A 2/2000 Campbell et al.
6,027,779 A 2/2000 Campbell et al.
6,027,811 A 2/2000 Campbell et al.
6,029,946 A 2/2000 Doyle
6,039,302 A 3/2000 Cote, Sr. et al.
6,039,714 A 3/2000 Cracauer et al.

(56) References Cited

U.S. PATENT DOCUMENTS

| | | | |
|---|---|---|---|
| 6,056,730 | A | 5/2000 | Greter |
| 6,056,731 | A | 5/2000 | Koetke et al. |
| 6,063,062 | A | 5/2000 | Paradis |
| 6,068,011 | A | 5/2000 | Paradis |
| 6,068,646 | A | 5/2000 | Lam |
| 6,070,767 | A | 6/2000 | Gardner et al. |
| 6,079,444 | A | 6/2000 | Harris et al. |
| 6,089,541 | A | 7/2000 | Weinheimer et al. |
| 6,093,154 | A | 7/2000 | Burek et al. |
| 6,103,695 | A | 8/2000 | Lane et al. |
| 6,106,502 | A | 8/2000 | Richmond |
| 6,106,503 | A | 8/2000 | Pfeiderer et al. |
| 6,113,068 | A | 9/2000 | Ryan |
| 6,117,114 | A | 9/2000 | Paradis |
| 6,120,264 | A | 9/2000 | Wang |
| 6,129,699 | A | 10/2000 | Haight et al. |
| 6,129,750 | A | 10/2000 | Tockman et al. |
| 6,132,403 | A | 10/2000 | Lopez |
| 6,132,407 | A | 10/2000 | Genese et al. |
| 6,149,129 | A | 11/2000 | Harris et al. |
| 6,156,004 | A | 12/2000 | Tremaine et al. |
| 6,165,217 | A | 12/2000 | Hayes |
| 6,168,137 | B1 | 1/2001 | Paradis |
| 6,170,800 | B1 | 1/2001 | Meloul et al. |
| 6,171,287 | B1 | 1/2001 | Lynn et al. |
| 6,193,682 | B1 | 2/2001 | Ahmed |
| 6,196,992 | B1 | 3/2001 | Keilman et al. |
| 6,200,292 | B1 | 3/2001 | French et al. |
| 6,217,556 | B1 | 4/2001 | Ellingson et al. |
| 6,221,425 | B1 | 4/2001 | Michal et al. |
| 6,231,507 | B1 | 5/2001 | Zikorus et al. |
| 6,234,992 | B1 | 5/2001 | Haight et al. |
| 6,234,996 | B1 | 5/2001 | Bagaoisan et al. |
| 6,235,009 | B1 | 5/2001 | Skow |
| 6,245,048 | B1 | 6/2001 | Fangrow, Jr. et al. |
| 6,254,061 | B1 | 7/2001 | Levine et al. |
| 6,254,581 | B1 | 7/2001 | Scott |
| 6,261,276 | B1 | 7/2001 | Reitsma |
| 6,261,282 | B1 | 7/2001 | Jepson et al. |
| 6,283,949 | B1 | 9/2001 | Roorda |
| 6,287,285 | B1 | 9/2001 | Michal et al. |
| 6,293,929 | B1 | 9/2001 | Smith et al. |
| 6,299,131 | B1 | 10/2001 | Ryan |
| 6,299,593 | B1 | 10/2001 | Wakabayashi |
| 6,309,423 | B2 | 10/2001 | Hayes |
| 6,319,235 | B1 | 11/2001 | Yoshimo |
| 6,328,765 | B1 | 12/2001 | Hardwick et al. |
| 6,332,892 | B1 | 12/2001 | Desmond, III et al. |
| 6,344,033 | B1 | 2/2002 | Jepson et al. |
| 6,352,525 | B1 | 3/2002 | Wakabayashi |
| 6,375,024 | B1 | 4/2002 | Park |
| 6,391,009 | B1 | 5/2002 | Crosa Dorado |
| 6,409,716 | B1 | 6/2002 | Sahatiian et al. |
| 6,428,520 | B1 | 8/2002 | Lopez et al. |
| 6,447,473 | B1 | 9/2002 | Levine et al. |
| 6,468,190 | B1 | 10/2002 | Fazio et al. |
| 6,482,190 | B1 | 11/2002 | Genese et al. |
| 6,491,668 | B1 | 12/2002 | Paradis |
| 6,500,164 | B1 | 12/2002 | Turner et al. |
| 6,530,951 | B1 | 3/2003 | Bates et al. |
| 6,541,116 | B2 | 4/2003 | Michal et al. |
| 6,551,267 | B1 | 4/2003 | Cohen et al. |
| 6,554,808 | B1 | 4/2003 | Cook |
| 6,562,013 | B1 | 5/2003 | Marasco, Jr. |
| RE38,145 | E | 6/2003 | Lynn |
| 6,620,132 | B1 | 9/2003 | Skow |
| 6,626,418 | B2 | 9/2003 | Kiehne et al. |
| 6,629,707 | B1 | 10/2003 | Yamaguchi et al. |
| 6,634,384 | B2 | 10/2003 | Skeens et al. |
| 6,635,020 | B2 | 10/2003 | Tripp, Jr. et al. |
| 6,637,726 | B1 | 10/2003 | Yamamoto |
| 6,641,562 | B1 | 11/2003 | Peterson |
| 6,641,574 | B2 | 11/2003 | Badia Segura et al. |
| 6,645,547 | B1 | 11/2003 | Shekalim et al. |
| 6,647,986 | B1 | 11/2003 | Korotko et al. |
| 6,651,956 | B2 | 11/2003 | Miller |
| 6,652,484 | B1 | 11/2003 | Hunckler et al. |
| 6,655,655 | B1 | 12/2003 | Matkovich et al. |
| 6,656,517 | B2 | 12/2003 | Michal et al. |
| 6,665,888 | B1 | 12/2003 | Kwak |
| 6,669,681 | B2 | 12/2003 | Jepson et al. |
| 6,673,049 | B2 | 1/2004 | Hommann et al. |
| 6,673,051 | B2 | 1/2004 | Flinchbaugh |
| 6,695,817 | B1 | 2/2004 | Fangrow, Jr. |
| 6,699,213 | B1 | 3/2004 | Annis et al. |
| 6,706,022 | B1 | 3/2004 | Leinsing et al. |
| 6,708,950 | B2 | 3/2004 | Christensen et al. |
| 6,719,991 | B2 | 4/2004 | Darouiche et al. |
| 6,726,672 | B1 | 4/2004 | Hanly et al. |
| 6,730,107 | B2 | 5/2004 | Kelley et al. |
| 6,733,000 | B2 | 5/2004 | McCarty et al. |
| 6,733,481 | B2 | 5/2004 | Ow |
| 6,745,998 | B2 | 6/2004 | Doyle |
| 6,755,391 | B2 | 6/2004 | Newton et al. |
| 6,780,497 | B1 | 8/2004 | Walter |
| 6,802,836 | B2 | 10/2004 | Bouphavichith et al. |
| 6,808,161 | B1 | 10/2004 | Hishikawa |
| D500,132 | S | 12/2004 | Peterson et al. |
| D500,133 | S | 12/2004 | Peterson et al. |
| 6,833,001 | B1 | 12/2004 | Chao |
| D500,552 | S | 1/2005 | Peterson et al. |
| D500,853 | S | 1/2005 | Peterson et al. |
| 6,840,501 | B2 | 1/2005 | Doyle |
| 6,849,061 | B2 | 2/2005 | Wagner |
| 6,896,665 | B2 | 5/2005 | Picha et al. |
| 6,897,349 | B2 | 5/2005 | Gibbins et al. |
| 6,916,379 | B2 | 7/2005 | Shekalim et al. |
| 6,936,031 | B2 | 8/2005 | Caleffi |
| 6,972,001 | B2 | 12/2005 | Emig et al. |
| 6,994,315 | B2 | 2/2006 | Ryan et al. |
| 7,004,923 | B2 | 2/2006 | Deniega et al. |
| 7,004,934 | B2 | 2/2006 | Vaillancourt |
| 7,008,407 | B1 | 3/2006 | Kamp |
| 7,044,441 | B2 | 5/2006 | Doyle |
| 7,048,724 | B2 | 5/2006 | Grossman et al. |
| 7,048,962 | B2 | 5/2006 | Shekalim et al. |
| 7,052,603 | B2 | 5/2006 | Schick |
| 7,090,191 | B2 | 8/2006 | Matkovich et al. |
| 7,094,218 | B2 | 8/2006 | Rome et al. |
| 7,100,890 | B2 | 9/2006 | Cote, Sr. et al. |
| 7,101,353 | B2 | 9/2006 | Lui et al. |
| 7,112,177 | B2 | 9/2006 | Christensen et al. |
| 7,150,740 | B2 | 12/2006 | Bennett et al. |
| 7,163,495 | B2 | 1/2007 | Fazio et al. |
| 7,165,568 | B2 | 1/2007 | Kessell et al. |
| 7,179,244 | B2 | 2/2007 | Smith et al. |
| 7,184,825 | B2 | 2/2007 | Leinsing et al. |
| 7,207,946 | B2 | 4/2007 | Sirokman |
| 7,303,553 | B2 | 12/2007 | Ott |
| 7,311,690 | B2 | 12/2007 | Burnett |
| 7,314,061 | B2 | 1/2008 | Peppel |
| 7,320,674 | B2 | 1/2008 | Ruddell et al. |
| 7,341,240 | B2 | 3/2008 | Ciesielka |
| 7,377,915 | B2 | 5/2008 | Rasmussen et al. |
| 7,383,073 | B1 | 6/2008 | Abovitz et al. |
| 7,396,348 | B2 | 7/2008 | Newton et al. |
| 7,401,703 | B2 | 7/2008 | McMichael et al. |
| 7,452,346 | B2 | 11/2008 | Axelsson |
| 7,452,354 | B2 | 11/2008 | Bright et al. |
| 7,468,058 | B2 | 12/2008 | Kanie et al. |
| 7,497,848 | B2 | 3/2009 | Leinsing et al. |
| 7,497,849 | B2 | 3/2009 | Fangrow, Jr. |
| 7,524,311 | B2 | 4/2009 | Phung et al. |
| 7,530,546 | B2 | 5/2009 | Ryan et al. |
| 7,547,302 | B2 | 6/2009 | Porto et al. |
| 7,563,243 | B2 | 7/2009 | Mendels |
| 7,569,045 | B2 | 8/2009 | Deniega et al. |
| 7,578,803 | B2 | 8/2009 | Rome et al. |
| 7,584,767 | B2 | 9/2009 | Funamura et al. |
| 7,591,805 | B2 | 9/2009 | Lampropoulos |
| 7,594,910 | B2 | 9/2009 | Butts et al. |
| 7,611,503 | B2 | 11/2009 | Spohn et al. |
| 7,614,123 | B2 | 11/2009 | Schweikert |
| 7,621,903 | B2 | 11/2009 | Delegge |

(56) References Cited

U.S. PATENT DOCUMENTS

| | | | |
|---|---|---|---|
| 7,628,774 | B2 | 12/2009 | Fangrow, Jr. |
| 7,628,779 | B2 | 12/2009 | Aneas |
| 7,632,260 | B2 | 12/2009 | Antoine |
| 7,637,893 | B2 | 12/2009 | Christensen et al. |
| 7,644,722 | B2 | 1/2010 | Christensen et al. |
| 7,674,248 | B2 | 3/2010 | Anderson et al. |
| 7,678,092 | B2 | 3/2010 | Matloub et al. |
| 7,682,332 | B2 | 3/2010 | Tanaka |
| 7,691,090 | B2 | 4/2010 | Belley et al. |
| 7,695,458 | B2 | 4/2010 | Belley et al. |
| 7,708,027 | B2 | 5/2010 | Yokota et al. |
| 7,717,891 | B1 | 5/2010 | Whaley |
| 7,726,315 | B2 | 6/2010 | Field |
| 7,726,328 | B2 | 6/2010 | Christensen et al. |
| 7,736,336 | B2 | 6/2010 | Plilshka et al. |
| 7,744,594 | B2 | 6/2010 | Yamazaki et al. |
| 7,758,574 | B2 | 7/2010 | Hijii et al. |
| 7,766,304 | B2 | 8/2010 | Phillips |
| 7,766,938 | B2 | 8/2010 | McGurk et al. |
| 7,780,612 | B2 | 8/2010 | Ross |
| 7,798,974 | B2 | 9/2010 | Sirokman |
| 7,815,168 | B2 | 10/2010 | Vangsness et al. |
| 7,824,384 | B2 | 11/2010 | Watson, Jr. |
| 7,833,194 | B2 | 11/2010 | Owens et al. |
| 7,854,731 | B2 | 12/2010 | Rome et al. |
| 7,857,284 | B2 | 12/2010 | Kimball et al. |
| 7,867,204 | B2 | 1/2011 | Bartholomew et al. |
| 7,879,012 | B2 | 2/2011 | Kane et al. |
| 7,892,181 | B2 | 2/2011 | Christensen et al. |
| 8,007,257 | B2 | 8/2011 | Heaton et al. |
| 8,048,046 | B2 | 11/2011 | Hudspeth et al. |
| 8,048,056 | B2 | 11/2011 | Picha et al. |
| 8,052,671 | B2 | 11/2011 | Christensen et al. |
| 8,057,448 | B2 | 11/2011 | Williams et al. |
| 8,074,848 | B2 | 12/2011 | Pittl et al. |
| 8,083,332 | B2 | 12/2011 | Price et al. |
| 8,147,417 | B2 | 4/2012 | Gavriely |
| 8,177,772 | B2 | 5/2012 | Christensen et al. |
| 8,210,166 | B2 | 7/2012 | Denton et al. |
| 8,224,422 | B2 | 7/2012 | Mottola et al. |
| 8,235,971 | B2 | 8/2012 | Christensen et al. |
| 8,246,590 | B2 | 8/2012 | Hu et al. |
| 8,337,475 | B2 | 12/2012 | Christensen et al. |
| 8,435,221 | B2 | 5/2013 | Hu et al. |
| 8,632,840 | B2 | 1/2014 | Avitable |
| 8,636,721 | B2 | 1/2014 | Alam et al. |
| 8,814,839 | B2 | 8/2014 | Christensen et al. |
| 8,845,680 | B2 | 9/2014 | Lampropoulos et al. |
| 9,295,764 | B2 | 3/2016 | Christensen et al. |
| 9,332,994 | B2 | 5/2016 | Pancholy et al. |
| 9,393,353 | B2 | 7/2016 | Alam et al. |
| D804,663 | S | 12/2017 | Jenkins |
| D821,590 | S | 6/2018 | Hylton et al. |
| 10,172,625 | B2 | 1/2019 | Wada et al. |
| 10,463,833 | B2 | 11/2019 | Clarke et al. |
| 10,492,797 | B2 | 12/2019 | Okamura |
| D893,034 | S | 8/2020 | Kase et al. |
| 2001/0047158 | A1 | 11/2001 | Ladd |
| 2002/0002351 | A1 | 1/2002 | Cote et al. |
| 2002/0123715 | A1 | 9/2002 | Sorenson et al. |
| 2002/0148467 | A1 | 10/2002 | Bosse et al. |
| 2002/0153503 | A1 | 10/2002 | Newton et al. |
| 2002/0188315 | A1 | 12/2002 | Guzman et al. |
| 2002/0198458 | A1 | 12/2002 | Tripp et al. |
| 2003/0017920 | A1 | 1/2003 | Fazio et al. |
| 2003/0032940 | A1 | 2/2003 | Doyle |
| 2003/0040769 | A1 | 2/2003 | Kelley et al. |
| 2003/0055453 | A1 | 3/2003 | Akerfeldt |
| 2003/0062498 | A1 | 4/2003 | Decler et al. |
| 2003/0111121 | A1 | 6/2003 | Skeens et al. |
| 2003/0139766 | A1 | 7/2003 | McEwen et al. |
| 2003/0149359 | A1 | 8/2003 | Smith |
| 2003/0159755 | A1 | 8/2003 | Wessberg |
| 2003/0165647 | A1 | 9/2003 | Kaneko et al. |
| 2003/0173536 | A1 | 9/2003 | Christensen et al. |
| 2004/0049157 | A1 | 3/2004 | Plishka et al. |
| 2004/0078026 | A1 | 4/2004 | Wagner |
| 2004/0082923 | A1 | 4/2004 | Field |
| 2004/0116894 | A1 | 6/2004 | Delegge |
| 2004/0215155 | A1 | 10/2004 | Wolfe et al. |
| 2004/0232696 | A1 | 11/2004 | Andre |
| 2004/0267163 | A1 | 12/2004 | Opie et al. |
| 2005/0025816 | A1 | 2/2005 | Tanaka |
| 2005/0090805 | A1 | 4/2005 | Shaw et al. |
| 2005/0113866 | A1 | 5/2005 | Heinz et al. |
| 2005/0121638 | A1 | 6/2005 | Doyle |
| 2005/0125025 | A1 | 6/2005 | Rioux |
| 2005/0131357 | A1 | 6/2005 | Denton et al. |
| 2005/0143691 | A1 | 6/2005 | Picha et al. |
| 2005/0203463 | A1 | 9/2005 | Lampropoulos |
| 2005/0203597 | A1 | 9/2005 | Yamazaki et al. |
| 2005/0209572 | A1 | 9/2005 | Rome et al. |
| 2005/0209581 | A1 | 9/2005 | Butts et al. |
| 2005/0251102 | A1 | 11/2005 | Hegland et al. |
| 2005/0261636 | A1 | 11/2005 | Rome et al. |
| 2005/0261664 | A1 | 11/2005 | Rome et al. |
| 2005/0267445 | A1 | 12/2005 | Mendels |
| 2005/0267487 | A1 | 12/2005 | Christensen et al. |
| 2005/0281822 | A1 | 12/2005 | Cedarbaum et al. |
| 2006/0009801 | A1 | 1/2006 | Mcgurk et al. |
| 2006/0015086 | A1 | 1/2006 | Rasmussen et al. |
| 2006/0058702 | A1 | 3/2006 | Christensen et al. |
| 2006/0058841 | A1 | 3/2006 | Mills et al. |
| 2006/0079853 | A1 | 4/2006 | Christensen et al. |
| 2006/0116721 | A1 | 6/2006 | Yun et al. |
| 2006/0118749 | A1 | 6/2006 | Ryan et al. |
| 2006/0129109 | A1 | 6/2006 | Shaw et al. |
| 2006/0190026 | A1 | 8/2006 | Sanders |
| 2006/0200089 | A1 | 9/2006 | Lopez et al. |
| 2006/0211998 | A1 | 9/2006 | Fangrow |
| 2006/0211999 | A1 | 9/2006 | Fangrow |
| 2006/0212000 | A1 | 9/2006 | Fangrow |
| 2006/0212001 | A1 | 9/2006 | Fangrow |
| 2006/0212002 | A1 | 9/2006 | Fangrow |
| 2006/0212003 | A1 | 9/2006 | Fangrow |
| 2006/0264842 | A1 | 11/2006 | Fangrow |
| 2007/0038143 | A1 | 2/2007 | Christensen et al. |
| 2007/0073270 | A1 | 3/2007 | Christensen et al. |
| 2007/0083157 | A1 | 4/2007 | Belley et al. |
| 2007/0083162 | A1 | 4/2007 | O'Reagan et al. |
| 2007/0100295 | A1 | 5/2007 | Belley et al. |
| 2007/0100322 | A1 | 5/2007 | Venugopalan et al. |
| 2007/0100324 | A1 | 5/2007 | Tempel et al. |
| 2007/0235674 | A1 | 10/2007 | Vangsness et al. |
| 2007/0235675 | A1 | 10/2007 | Kimball et al. |
| 2007/0235676 | A1 | 10/2007 | Vangsness et al. |
| 2007/0239092 | A1 | 10/2007 | Ross |
| 2007/0248810 | A1 | 10/2007 | Mcgee et al. |
| 2007/0255167 | A1 | 11/2007 | Christensen et al. |
| 2007/0255229 | A1 | 11/2007 | Kane et al. |
| 2007/0260195 | A1 | 11/2007 | Bartholomew et al. |
| 2007/0270720 | A1 | 11/2007 | Fry |
| 2007/0270764 | A1 | 11/2007 | Gordon |
| 2007/0282268 | A1 | 12/2007 | Mayse |
| 2008/0091174 | A1 | 4/2008 | Alam et al. |
| 2008/0097407 | A1 | 4/2008 | Plishka |
| 2008/0103408 | A1 | 5/2008 | Denton et al. |
| 2008/0114316 | A1 | 5/2008 | Christensen et al. |
| 2008/0177175 | A1 | 7/2008 | Mottola et al. |
| 2008/0277610 | A1 | 11/2008 | Bahner et al. |
| 2009/0012493 | A1 | 1/2009 | Harig |
| 2009/0043270 | A1 | 2/2009 | Noyce et al. |
| 2009/0069763 | A1 | 3/2009 | DiCarlo et al. |
| 2009/0142741 | A1 | 6/2009 | Ault et al. |
| 2009/0209896 | A1 | 8/2009 | Selevan |
| 2009/0219353 | A1 | 9/2009 | Price et al. |
| 2009/0240182 | A1 | 9/2009 | Weber et al. |
| 2009/0261130 | A1 | 10/2009 | Pittl et al. |
| 2009/0281565 | A1* | 11/2009 | McNeese ........... A61B 17/1325 606/201 |
| 2009/0312725 | A1 | 12/2009 | Braga |
| 2009/0314973 | A1 | 12/2009 | Christensen et al. |
| 2010/0030163 | A1 | 2/2010 | Carrez et al. |
| 2010/0044609 | A1 | 2/2010 | Matsubara |

(56) References Cited

U.S. PATENT DOCUMENTS

2010/0211000 A1 8/2010 Killion et al.
2010/0217202 A1 8/2010 Clark
2010/0274229 A1 10/2010 Duocastella Codina et al.
2010/0280541 A1 11/2010 Lampropoulos
2011/0009849 A1 1/2011 Christensen et al.
2011/0022012 A1 1/2011 Kerr et al.
2011/0071415 A1 3/2011 Karwoski et al.
2011/0083665 A1 4/2011 Denton et al.
2011/0105963 A1 5/2011 Hu et al.
2011/0172510 A1 7/2011 Chickering, III
2011/0238022 A1 9/2011 Massi et al.
2011/0275964 A1 11/2011 Greener
2011/0276017 A1 11/2011 Schuessler et al.
2012/0220984 A1 8/2012 Christensen et al.
2012/0221041 A1* 8/2012 Hansson .............. A61B 17/135 606/203
2012/0238934 A1 9/2012 During
2012/0296369 A1 11/2012 Atthoff et al.
2013/0023734 A1 1/2013 Okamura
2013/0079723 A1 3/2013 Andino et al.
2013/0090614 A1 4/2013 Christensen et al.
2013/0165787 A1 6/2013 Ukawa et al.
2013/0237866 A1 9/2013 Cohen
2013/0245675 A1 9/2013 Wada et al.
2013/0289613 A1 10/2013 Wada et al.
2014/0012120 A1 1/2014 Cohen et al.
2014/0012313 A1 1/2014 Finkielsztien et al.
2014/0142615 A1 5/2014 Corrigan, Jr.
2014/0182594 A1 7/2014 Alam et al.
2014/0236221 A1 8/2014 Zhadkevich
2014/0288408 A1 9/2014 Deutsch
2014/0358095 A1 12/2014 Christensen et al.
2015/0018868 A1 1/2015 Pancholy
2015/0018869 A1 1/2015 Benz et al.
2015/0032149 A1 1/2015 Croushorn et al.
2015/0119925 A1 4/2015 Saatchi et al.
2015/0164436 A1 6/2015 Maron et al.
2015/0201948 A1 7/2015 Kornowski et al.
2015/0314074 A1 11/2015 Howlett et al.
2015/0327870 A1 11/2015 Fortson et al.
2015/0327871 A1 11/2015 Fortson et al.
2015/0342615 A1 12/2015 Keinan et al.
2016/0058988 A1 3/2016 Kesten et al.
2016/0095605 A1 4/2016 Maris
2016/0101269 A1 4/2016 Benz
2016/0183951 A1 6/2016 Pancholy
2016/0279395 A1 9/2016 Lampropoulos et al.
2017/0000988 A1 1/2017 Stevens et al.
2017/0007807 A1 1/2017 Weerakoon et al.
2017/0273693 A1 9/2017 Morrison et al.
2017/0354336 A1* 12/2017 Dang ..................... A61H 39/04
2018/0000494 A1 1/2018 Wada et al.
2018/0008281 A1 1/2018 Hazama
2018/0008282 A1 1/2018 Hazama et al.
2018/0008283 A1 1/2018 Hazama
2018/0014832 A1 1/2018 Lampropoulos et al.
2018/0028195 A1 2/2018 Benz et al.
2018/0042615 A1 2/2018 Kimura et al.
2018/0070956 A1 3/2018 Lampropoulos et al.
2018/0185032 A1 7/2018 Matsushita et al.
2018/0250017 A1 9/2018 Matsushita et al.
2018/0280008 A1 10/2018 Okamura
2019/0021742 A1 1/2019 Hazama
2019/0029693 A1 1/2019 Okamura
2019/0046214 A1 2/2019 Hazama
2019/0090886 A1 3/2019 Brown et al.
2019/0133602 A1 5/2019 Kiemeneij et al.
2019/0133604 A1 5/2019 Maeda et al.
2019/0133605 A1 5/2019 Hazama et al.
2019/0133606 A1 5/2019 Hazama
2019/0133607 A1 5/2019 Hazama
2019/0150938 A1 5/2019 Hazama et al.
2019/0167273 A1* 6/2019 Morrison ............. A61B 17/135
2019/0274692 A1 9/2019 Lampropoulos et al.
2019/0314035 A1 10/2019 Hopkinson et al.
2020/0029946 A1 1/2020 Green et al.
2021/0052282 A1 2/2021 Lampropoulos et al.
2022/0370080 A1 11/2022 Kiemeneij et al.
2022/0401086 A1 12/2022 Stephenson et al.
2023/0255640 A1 8/2023 Monroe et al.

FOREIGN PATENT DOCUMENTS

CN 201861701 6/2011
CN 107224310 A 10/2017
CN 208864401 5/2019
CN 209695299 11/2019
DE 1616493 6/1971
DE 4006696 11/1990
DE 9105229 6/1991
DE 4311715 10/1994
EP 0270205 6/1988
EP 0829248 3/1998
EP 1547537 6/2005
EP 1684824 8/2006
EP 1740253 1/2007
EP 1782850 5/2007
FR 2551978 3/1985
FR 2828231 2/2003
GB 2109239 6/1983
GB 2394761 5/2004
JP 2002049660 2/1990
JP 2005115556 5/1993
JP H6504468 5/1994
JP H666642 9/1994
JP 1995047071 2/1995
JP 2000517216 12/2000
JP 2002177379 6/2002
JP 2012010823 1/2012
JP 2013042859 3/2013
JP 2013111444 6/2013
JP 6211285 10/2014
JP 2014200308 10/2014
JP 6261368 8/2015
JP 2015150298 8/2015
JP 6389510 9/2015
JP 6261420 11/2015
JP 2015188608 11/2015
JP 2017000259 1/2017
JP 2017000260 1/2017
JP 2017047036 3/2017
JP 2018011798 1/2018
JP 2018011867 1/2018
JP 2018019927 2/2018
JP 2018033602 3/2018
JP 2018075257 5/2018
JP 2018171081 11/2018
JP 2019047956 3/2019
JP 2019058498 4/2019
JP 6544854 6/2019
JP 6559128 7/2019
JP 2019154915 9/2019
JP 2019166265 10/2019
JP 2019208953 12/2019
JP 2019216947 12/2019
JP 2019217130 12/2019
JP 2020014588 1/2020
JP 6667234 2/2020
JP 2020018686 2/2020
JP 2020022679 2/2020
JP 2020039815 3/2020
JP 2020039816 3/2020
WO 1990003194 4/1990
WO 1992007591 5/1992
WO 1995001135 1/1995
WO 199855072 12/1998
WO 1999011192 3/1999
WO 200204065 1/2002
WO 2003001993 1/2003
WO 2003018105 3/2003
WO 2004041313 5/2004
WO 2005007213 1/2005
WO 2005044716 5/2005
WO 2005052366 6/2005

(56) References Cited

FOREIGN PATENT DOCUMENTS

| | | | |
|---|---|---|---|
| WO | 2005099805 | | 10/2005 |
| WO | 2005107843 | | 11/2005 |
| WO | 2006004943 | | 1/2006 |
| WO | 2006055288 | | 5/2006 |
| WO | 2006060248 | | 6/2006 |
| WO | 2006066023 | | 6/2006 |
| WO | 2007038643 | | 4/2007 |
| WO | 2007116386 | | 10/2007 |
| WO | 2008115439 | | 9/2008 |
| WO | 2008142580 | | 11/2008 |
| WO | 2009027665 | | 3/2009 |
| WO | 2009081180 | | 7/2009 |
| WO | 2009118521 | | 10/2009 |
| WO | 2010028044 | | 3/2010 |
| WO | 2010091356 | | 8/2010 |
| WO | 2011107972 | | 9/2011 |
| WO | 2015141786 | | 9/2015 |
| WO | 2015183470 | A2 | 12/2015 |
| WO | 2016118695 | | 7/2016 |
| WO | 2017043536 | | 3/2017 |
| WO | 2018008602 | A1 | 1/2018 |
| WO | 2018017365 | | 1/2018 |

OTHER PUBLICATIONS

Mabry, et al., United States Army Rangers in Somalia: An Analysis of Combat Casualties on an Urban Battlefield, J. Trauma, vol. 49 No. 3 ,Sep. 2000 ,515-529.
Medcompare, et al., Drains with Reservoirs, General Surgery Product Matrix, Medcompare.com/matrix/1885/Drains-with-Reservoirs.html, Copyright ,2003-2010 ,198-202.
Milton Jr., et al., Urban Operations: Future War, Military Review, vol. 74 Issue 2 ,Feb. 1994.
Montes, et al., Influence of Talc Dos on Extrapleural Talc Dissemination after Talc Pleurodesis, Am. J. Respir, Crit. Care Med., vol. 168 No. 3 ,2003 ,348-355.
Ohm, et al., Use of Indwelling Pleural Catheter Compared withThorascopic Talc Pleurodesis in the Management of Malignant Pleural Effusions, Division of Thoracic Surgery and Department of Surgery, William Beaumont Hospital, The American Surgeon, vol. 69 ,Mar. 2003 ,198-202.
Pope, et al., Fluid Resuscitation: State fo the Science for Treating Combat Casualties and Civilian Injuries, National Academy Press ,1999.
Pua, et al., "Snuffbox" Distal Radial Access, J Vasc Interv Radiol, No. 29:44 ,2018.
Schweitzer, et al., Use of Heimlich Valve in compact Autotransfusion Device, The Journal of Trauma, vol. 27 No. 5 , 1987 ,537-542.
Tremblay, et al., Singel-Center Experience with 250 Tunnelled Pleural Catheter Insertions for Manignant Pleural Effusions, Chest, vol. 129 No. 2 ,2006 ,362-368.
Vargas, et al., Comparison of Silver Nitrate and Tetracycline as Pleural Sclerosing Agents in Rabbits, Chest, vol. 108 No. 4 , 1995 ,1080-1083.
Vargas, et al., Experimental Plerueodesis in Rabbits Induced by Silver Nitrate or Talc, ASAP, vol. 199 No. 5 ,May 1, 2001 ,1516.
Zhou, et al., Transient Ulnar Artery Compression Facilitates Transradial Access, Medicine, No. 95:48 ,2016.
Notice of Allowance dated Oct. 5, 2022 for U.S. Appl. No. 16/380,505.
Office Action dated Dec. 10, 2014 for U.S. Appl. No. 12/188,955.
Office Action dated Jun. 6, 2016 for U.S. Appl. No. 14/033,177.
Office Action dated Jun. 9, 2015 for U.S. Appl. No. 14/464,503.
Office Action dated Jun. 12, 2013 for U.S. Appl. No. 10/595,450.
Office Action dated Jun. 28, 2011 for U.S. Appl. No. 12/349,405.
Office Action dated Jun. 29, 2009 for U.S. Appl. No. 11/248,082.
Office Action dated Jul. 6, 2011 for U.S. Appl. No. 11/248,082.
Office Action dated Jul. 13, 2012 for U.S. Appl. No. 12/188,955.
Office Action dated Jul. 17, 2009 for U.S. Appl. No. 10/595,450.
Office Action dated Jul. 23, 2021 for U.S. Appl. No. 16/179,257.
Office Action dated Jul. 25, 2017 for U.S. Appl. No. 15/081,783.
Office Action dated Aug. 1, 2012 for U.S. Appl. No. 13/469,849.
Office Action dated Aug. 2, 2013 for U.S. Appl. No. 13/688,000.
Office Action dated Aug. 17, 2012 for U.S. Appl. No. 12/349,405.
Office Action dated Aug. 23, 2011 for U.S. Appl. No. 12/879,673.
Office Action dated Sep. 6, 2019 for U.S. Appl. No. 15/705,759.
Office Action dated Sep. 14, 2021 for U.S. Appl. No. 16/921,343.
Office Action dated Sep. 16, 2020 for U.S. Appl. No. 16/380,505.
Office Action dated Sep. 18, 2015 for U.S. Appl. No. 14/464,503.
Office Action dated Oct. 1, 2010 for U.S. Appl. No. 10/595,450.
Office Action dated Oct. 6, 2015 for U.S. Appl. No. 12/188,955.
Office Action dated Oct. 8, 2020 for U.S. Appl. No. 16/179,257.
Office Action dated Oct. 10, 2018 for U.S. Appl. No. 15/912,244.
Office Action dated Oct. 12, 2010 for U.S. Appl. No. 11/535,245.
Office Action dated Oct. 30, 2008 for U.S. Appl. No. 10/595,450.
Office Action dated Oct. 30, 2008 for U.S. Appl. No. 11/248,082.
Office Action dated Oct. 30, 2015 for U.S. Appl. No. 14/162,654.
Office Action dated Nov. 3, 2015 for U.S. Appl. No. 14/033,177.
Office Action dated Nov. 6, 2013 for U.S. Appl. No. 12/188,955.
Office Action dated Dec. 8, 2011 for U.S. Appl. No. 12/349,405.
Office Action dated Dec. 21, 2010 for U.S. Appl. No. 11/248,082.
Office Action dated Dec. 24, 2013 for U.S. Appl. No. 13/688,000.
Office Action dated Dec. 27, 2016 for U.S. Appl. No. 14/033,177.
Office Action dated Jul. 7, 2011 for U.S. Appl. No. 11/535,245.
AstraTech Healthcare, 'Premimun Wound Drainage Products', http://surgery.astratech.com/Main.aspx?Item-155788&navl=5&navl=82118&nava=81296, Copyright ,2010.
Bard Access Systems, Inc., 'Poly Per-Q-Cath PICC Catheter with Safety Excalibur Introducer', Instructions for Use, , May 2003.
Bard, 'Groshong NXT PICC Instructions for Use', Product Brochure, ,Nov. 2003.
ICU-USA, 'Wound Drainage', www.icu-usa.com/tour/procedures/drains.htm, Copyright 1999-2004.
Management of Malignant Pleural Effusions, Am. J. Respir. Crit. Care Med., vol. 165 No. 5 ,2000 , 1987-2001.
Merit Medical Adds 2 New Products for Assisting Hemostasis, Posted at Merit.com, no posting date, retrieved Aug. 26, 2020 online https://www.merit.com/articles/merit-medical-adds-2-new-products-assisting-hemostasis (2020).
Pleural Disease-Diagnosis and Management, The Practitioner ,May 1999 ,412.
Pleurodesis, ASAP, vol. 118, No. 3 ,Sep. 1, 2000 ,577.
Bellamy, et al., The Causes of Death in Conventional Land Warfare: Implications for combat Casualty Care Research, Mil. Med., vol. 149 ,1984 ,55-62.
Bilski, et al., Battlefield Casualties Treated at Camp Rhino, Afghanistan: Lessons Learned, J. Trauma, vol. 54 No. 5 , May 2003 ,814-822.
Campisi, et al., Outpatient Treatment of Spontaneous Pheumothorax in a Community Hospital Using a Heimlich Flutter Valve: A Case Series, The Journal of Emergency Medicine, vol. 15 No. 1 , 1997 , 115-119.
Groves Jr., et al., Operations in Urban Environments, Military Review, vol. 78 No. 4 ,Jul./Aug. 1998.
Heimlich, et al., Valve Drainage of the Pleural Cavity, Diseases of the Chest, vol. 53 No. 3 ,1968 ,282-287.
Hewitt, et al., A Management Strategy for Malignancy-Induced Pleural Effusion: Long-Term Thoracostomy Drainage, ONF, vol. 14 No. 5 ,1987 ,17-22.
Jaskille, et al., A Portable Handpump is Effective inthe Evacuation of Hemothorax in a Swine Model of Penetratine Chest Injury, The Journal of Trauma Injury, Infection, and Critical Care ,Nov. 2003 , 864-868.
Light,R.W. et al., A Single Intrapleural Injection of Transforming Growth Factor-Beta(2) Produces an Excellent Pleurodesis in Rabbits, Am. J. Respir. Crit. Care Med., vol. 162 No. 1,2000 ,98-104.
Light, et al., Talc Slurry is an Effective Pleural Sclerosant in Rabbits, Chest, vol. 106 No. 6 ,1995 ,1702-1706.
European Search Report dated Feb. 27, 2020 for EP17851579.7.
European Search Report dated Apr. 23, 2021 for EP18872642.6.
European Search Report dated Jul. 9, 2021 for EP18876110.0.
European Search Report dated Sep. 7, 2017 for EP 09763115.4.
European Search Report dated Nov. 23, 2021 for EP19784978.9.

(56) References Cited

OTHER PUBLICATIONS

European Supplemental Search Report dated Aug. 17, 2012 for EP04811627.1.
Extended European Search Report dated Oct. 28, 2021 for EP19763606.1.
International Search Report and Written Opinion dated Jan. 5, 2007 for PCT/US2006/037766.
International Search Report and Written Opinion dated Jan. 25, 2007 for PCT/US2006/037766.
International Search Report and Written Opinion dated Apr. 2, 2019 for PCT/US2018/060089.
International Search Report and Written Opinion dated May 14, 2019 for PCT/US2018/058992.
International Search Report and Written Opinion dated Jun. 12, 2019 for PCT/US2019/020980.
International Search Report and Written Opinion dated Jul. 5, 2005 for PCT/US2004/38937.
International Search Report and Written Opinion dated Jul. 30, 2019 for PCT/US2019/026785.
International Search Report and Written Opinion dated Nov. 28, 2017 for PCT/US2017/041726.
International Search Report and Written Opinion dated Dec. 26, 2017 for PCT/US2017/051715.
International Search Report dated Nov. 18, 2009 for PCT/US2009/042868.
MedPlus, Inc., Tourniquet (Radial Artery Compression Device), http://www.bikudo.com/product_search/details/187473/tourniquet_radial_artey_compression_device.html Nov. 24, 2009.
Notice of Allowance dated Jan. 12, 2010 for U.S. Appl. No. 11/248,082.
Notice of Allowance dated Apr. 12, 2010 for U.S. Appl. No. 11/248,082.
Notice of Allowance dated Apr. 30, 2014 for U.S. Appl. No. 13/688,000.
Notice of Allowance dated Jun. 9, 2014 for U.S. Appl. No. 13/741,046.
Notice of Allowance dated Jun. 10, 2013 for U.S. Appl. No. 13/469,849.
Notice of Allowance dated Sep. 9, 2021 for U.S. Appl. No. 16/294,020.
Notice of Allowance dated Sep. 17, 2012 for U.S. Appl. No. 11/248,082.
Notice of Allowance dated Oct. 15, 2010 for U.S. Appl. No. 11/248,082.
Notice of Allowance dated Oct. 16, 2012 for U.S. Appl. No. 12/435,227.
Notice of Allowance dated Nov. 22, 2021 for U.S. Appl. No. 16/179,257.
Notice of Allowance dated Nov. 25, 2020 for U.S. Appl. No. 29/653,828.
Notice of Allowance dated Nov. 30, 2015 for U.S. Appl. No. 14/464,503.
Office Action dated Jan. 8, 2020 for U.S. Appl. No. 15/648,110.
Office Action dated Jan. 10, 2019 for U.S. Appl. No. 15/705,759.
Office Action dated Jan. 11, 2012 for U.S. Appl. No. 12/188,955.
Office Action dated Feb. 1, 2011 for U.S. Appl. No. 12/879,673.
Office Action dated Feb. 14, 2014 for U.S. Appl. No. 13/741,046.
Office Action dated Feb. 16, 2021 for U.S. Appl. No. 16/380,505.
Office Action dated Mar. 2, 2011 for U.S. Appl. No. 12/349,405.
Office Action dated Mar. 5, 2013 for U.S. Appl. No. 13/741,046.
Office Action dated Mar. 17, 2011 for U.S. Appl. No. 11/535,245.
Office Action dated Mar. 28, 2012 for U.S. Appl. No. 11/248,082.
Office Action dated Mar. 29, 2013 for U.S. Appl. No. 12/188,955.
Office Action dated Mar. 30, 2010 for U.S. Appl. No. 11/248,082.
Office Action dated Apr. 12, 2021 for U.S. Appl. No. 16/179,257.
Office Action dated Apr. 23, 2013 for U.S. Appl. No. 13/677,000.
Office Action dated May 2, 2014 for U.S. Appl. No. 12/188,955.
Office Action dated May 4, 2016 for U.S. Appl. No. 12/188,955.
Office Action dated May 10, 2021 for U.S. Appl. No. 16/294,020.
Office Action dated May 25, 2021 for U.S. Appl. No. 16/380,505.
Office Action dated May 26, 2011 for U.S. Appl. No. 12/188,955.
Office Action dated May 28, 2019 for U.S. Appl. No. 15/648,110.
International Search Report and Written Opinion dated Nov. 30, 2021 for PCT/US2021/045607.
Notice of Allowance dated Feb. 3, 2022 for U.S. Appl. No. 16/921,343.
European Examination Report dated Oct. 9, 2023 for EP19763606.1.
European Search Report dated Jun. 13, 2024 for EP21856668.5.
Office Action dated Apr. 5, 2022 for U.S. Appl. No. 16/380,505.
European Examination Report dated Jun. 26, 2024 for EP18872642.6.
Office Action dated Feb. 10, 2025 for U.S. Appl. No. 17/657,067.
Pyles, et al., "Cannulation of the Dorsal Radial Artery: A New Technique", Anesthesia and Analgesia, vol. 61, No. 10, Oct. 1982, 3 pgs.
Office Action dated Jul. 14, 2025 for U.S. Appl. No. 17/657,067.
Office Action dated Jul. 21, 2025 for U.S. Appl. No. 18/166,721.

* cited by examiner

INFLATABLE RADIAL ARTERY COMPRESSION DEVICE WITH CINCHING WRISTBAND AND METHOD OF USE

RELATED APPLICATION

This application claims priority to U.S. Provisional Application No. 63/065,318, filed on Aug. 13, 2020, and titled “INFLATABLE RADIAL ARTERY COMPRESSION DEVICE WITH CINCHING WRISTBAND AND METHOD OF USE” which is hereby incorporated by reference in its entirety.

TECHNICAL FIELD

The present disclosure relates generally to the field of medical devices. More particularly, some embodiments relate to compression devices, including radial artery compression devices with an inflatable chamber and a cinching wristband.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
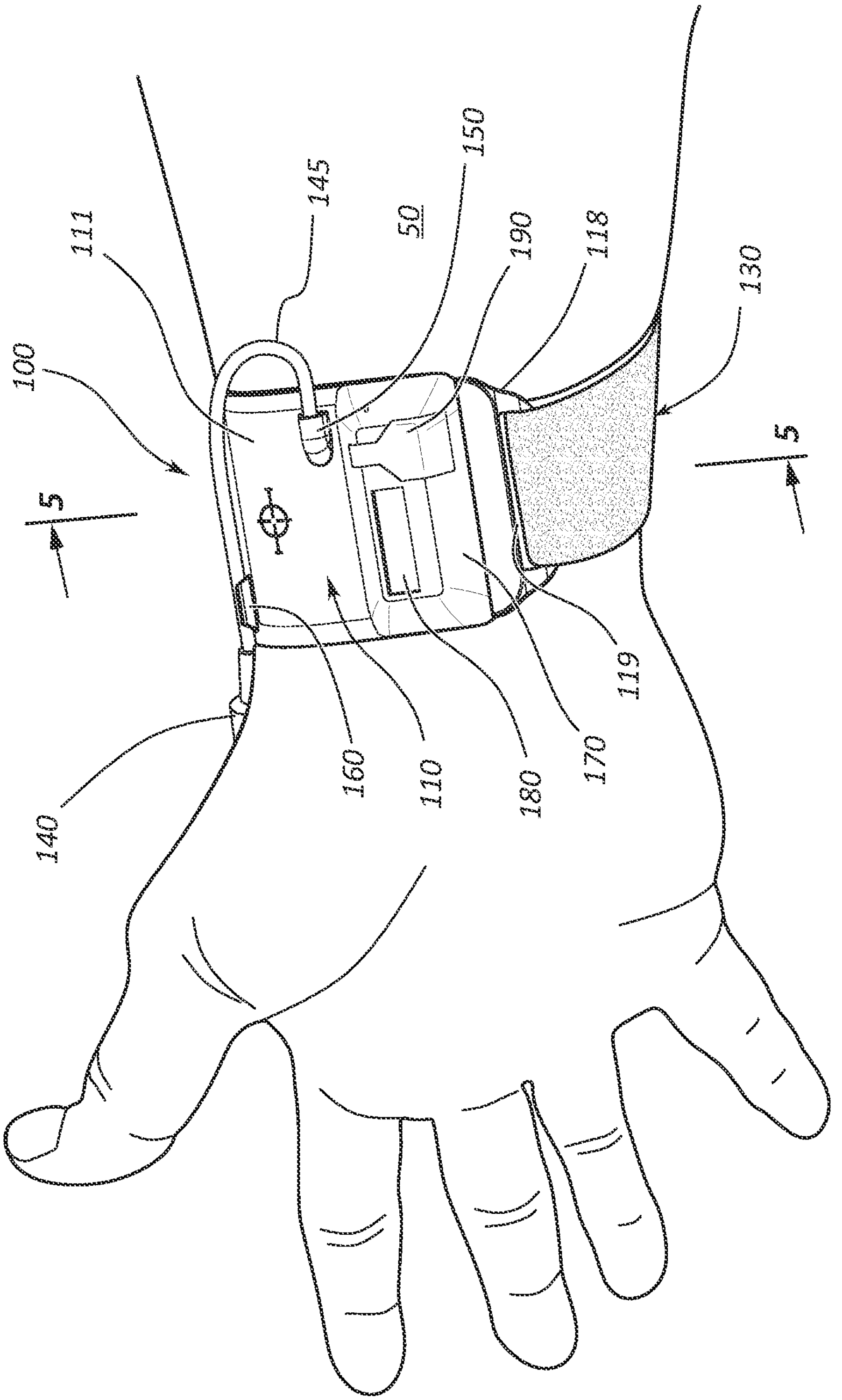
FIG. 1 depicts an embodiment of a radial artery compression device that is secured to a wrist of a patient.

Various medical procedures involve insertion of one or more elongate medical devices into the vasculature of a patient. Some such interventional procedures involve delivery of a medical device through a radial artery of the patient. Achieving hemostasis during and/or after an interventional procedure that involves puncturing the vasculature may be facilitated by compression. In certain embodiments within the scope of this disclosure, relate to compression devices configured to compress the radial artery of a patient. Use of such devices, or analogous devices, to provide compression along other portions of the vasculature, including vasculature within the arm, leg, or other parts of the human body are likewise within the scope of this disclosure. Accordingly, disclosure recited herein in connection with compression of the radial artery may be analogously applied to devices configured to compress other portions of the vasculature.

To facilitate hemostasis at the radial access site, pressure may be applied at an arteriotomy site which may be slightly upstream of the skin puncture site. Such pressure may prevent or reduce the leakage of blood from the arteriotomy site and promote hemostasis. Certain embodiments described herein facilitate the application of pressure to promote hemostasis at a radial access site.

The application of devices that wrap around an extremity such as a wrist may in some instances present various difficulties for a medical practitioner. Compression devices for hemostasis may present a discomfort for the patient. Compression devices that are secured around an extremity such as a wrist may be configured to minimize such discomfort by controlling the tension on a strap of the compression device, i.e., sufficient tension to cause the compression device to apply the pressure to facilitate hemostasis while minimizing or avoiding tension that results in unnecessary or undesired constriction. Establishing and maintaining an accurate placement of a hemostasis device over an arteriotomy site or skin puncture site while creating a desired amount of tension may, in some instances, present challenges for the medical practitioner. The use of hook and loop fastening systems may facilitate a continuous range of attachment lengths correlating to range of patient sizes. Hook and loop fastening systems may also be an economical fastening solution. However, hook and loop fastening systems comprising two separate bands each having a free end, one band with the hook components and the other band with the loops may complicate fastening of the bands. For example, coupling two separate bands, each with a free end, may require two hands and/or may be difficult or awkward to couple together while maintaining a desired placement and/or amount of tension. As described herein, compression devices comprising a band with both hook and loop components associated with one band having one free end, may facilitate coupling, placement, and tensioning the compression device on a patient.

The components of the embodiments as generally described and illustrated in the figures herein can be arranged and designed in a wide variety of different configurations. Thus, the following more detailed description of various embodiments, as represented in the figures, is not intended to limit the scope of the present disclosure but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to one another through an intermediate component. The phrase "attached to" refers to interactions between two or more entities that are in direct contact with each other and/or are separated from each other only by a fastener of any suitable variety (e.g., an adhesive). The phrase "fluid communication" is used in its ordinary sense and is broad enough to refer to arrangements in which a fluid (e.g., a gas or a liquid) can flow from one element to another element when the elements are in fluid communication with each other.

The terms "proximal" and "distal" are opposite directional terms and are given their ordinary meaning in the medical device field. That is, these terms are used to indicate direction on medical devices, or portions of medical devices, where one end—designated the proximal end—is nearest a practitioner during regular use. Additionally, this disclosure uses the terms radial and ulnar to refer to directions along the arm of a patient. When used as a directional term, the term "radial" refers to the direction pointing from the center of the arm or hand to the thumb-side portion of the arm or hand. The term "ulnar" refers to the opposite direction. The particular volumes recited herein refer to the volumes of fluid that are delivered from a syringe that holds the recited amount of fluid at atmospheric pressure. For example, an inflatable chamber has a capacity of 15 mL if it is capable of receiving 15 mL of air from a syringe that holds 15 mL of air at atmospheric pressure.

Figure 2:
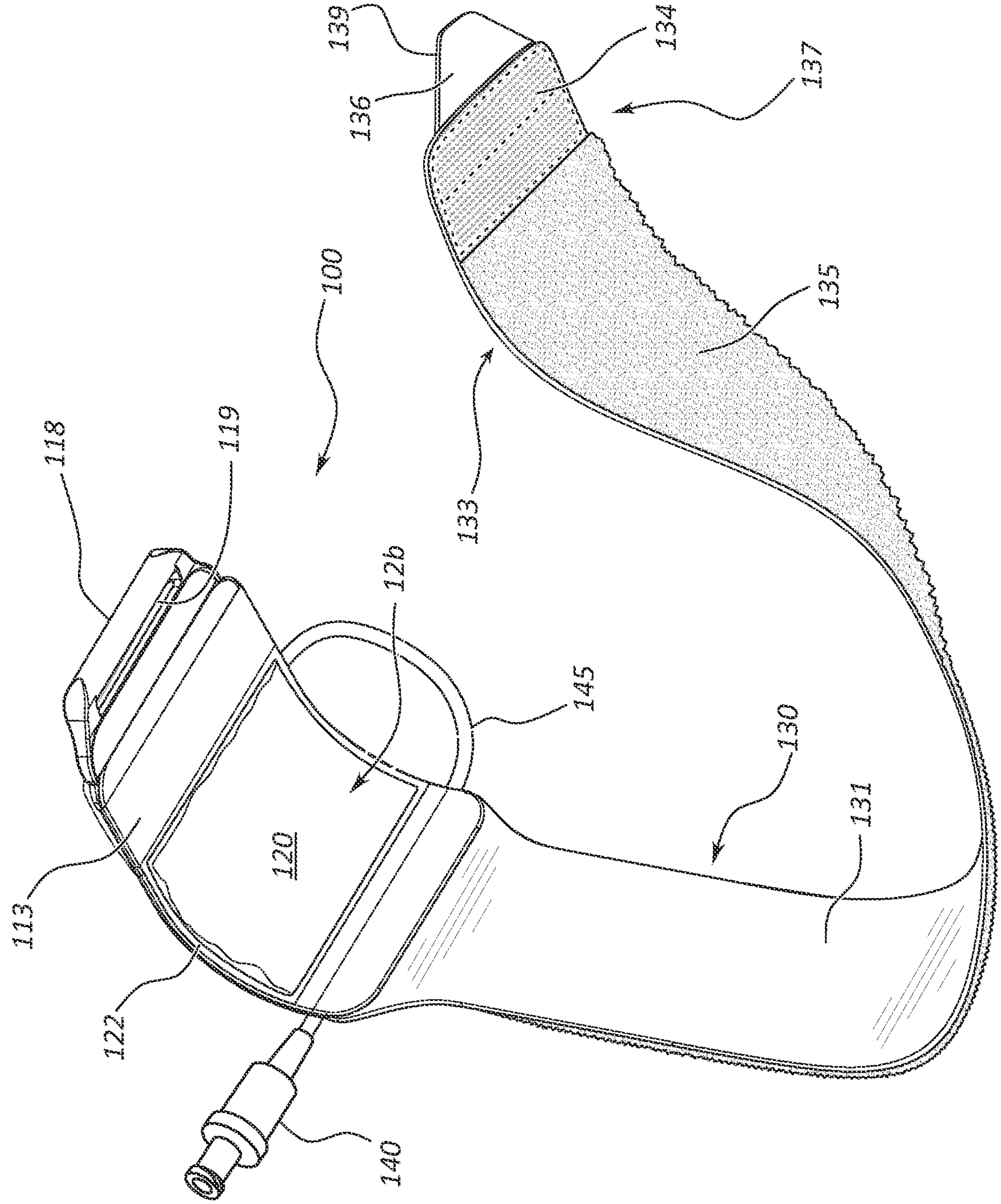
FIG. 2 is a perspective view of an underside of the radial artery compression device of FIG. 1.
Figure 3A:
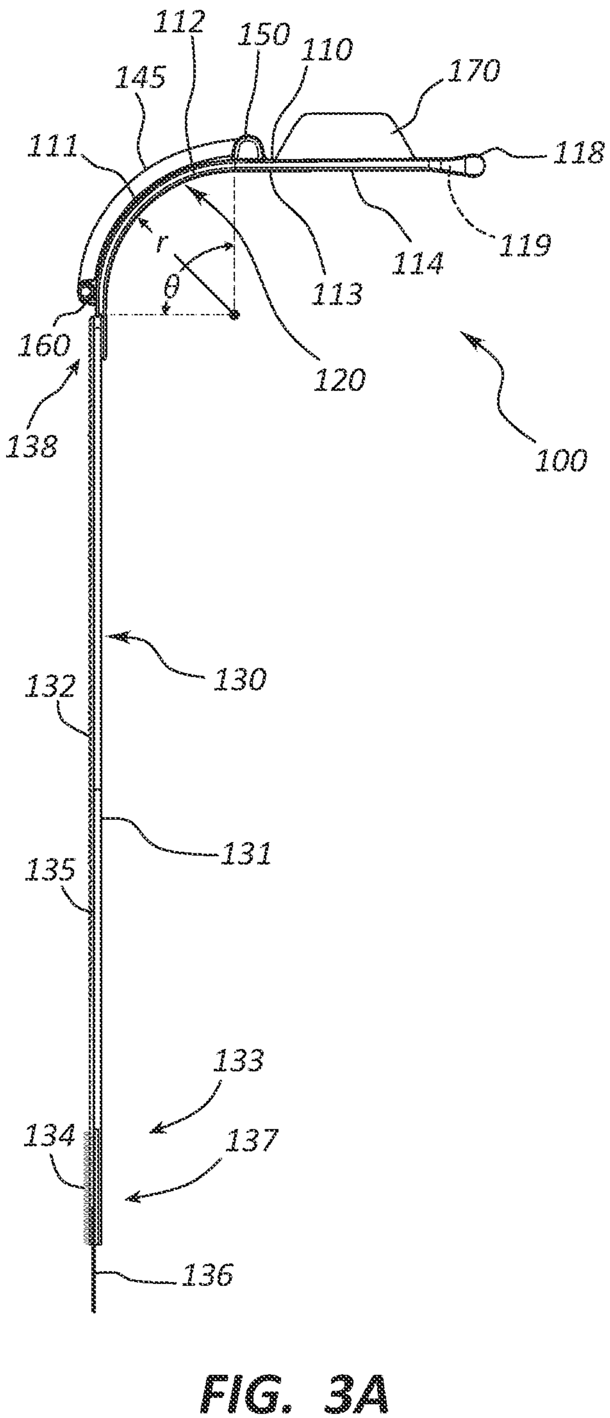
FIG. 3A is a side view of the radial artery compression device of FIGS. 1-2 with the inflatable chamber in an uninflated state.
Figure 3B:
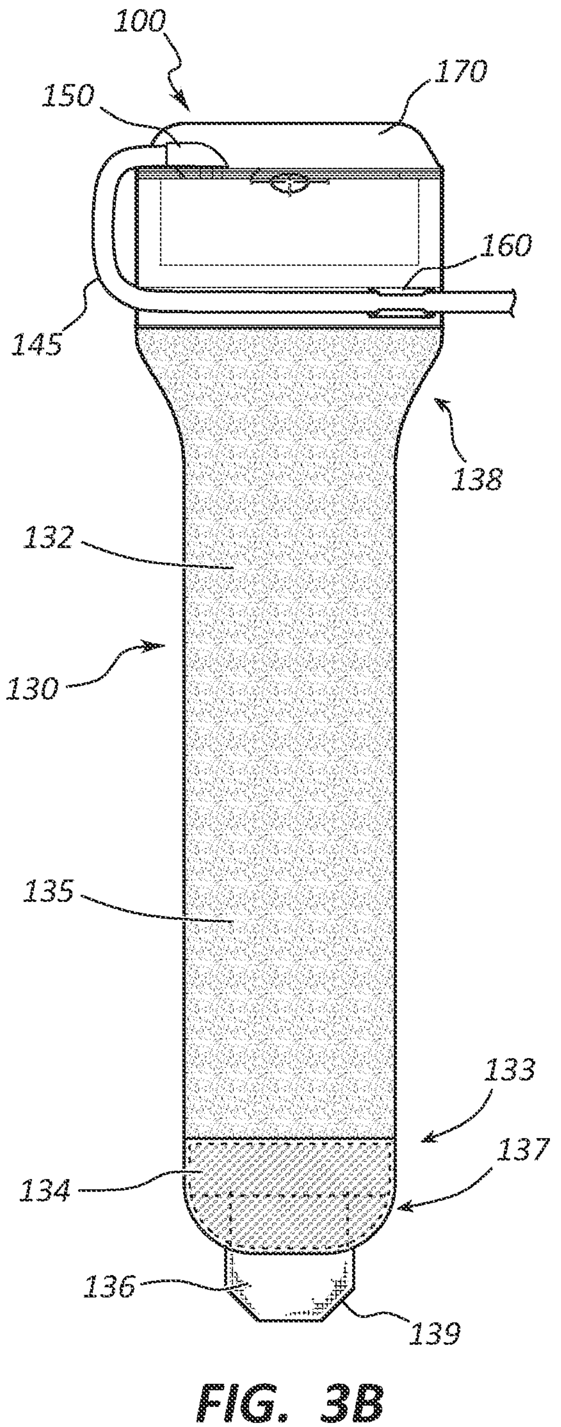
FIG. 3B is a front view of the radial artery compression device of FIGS. 1-2 showing the outer side of the wristband.
Figure 4:
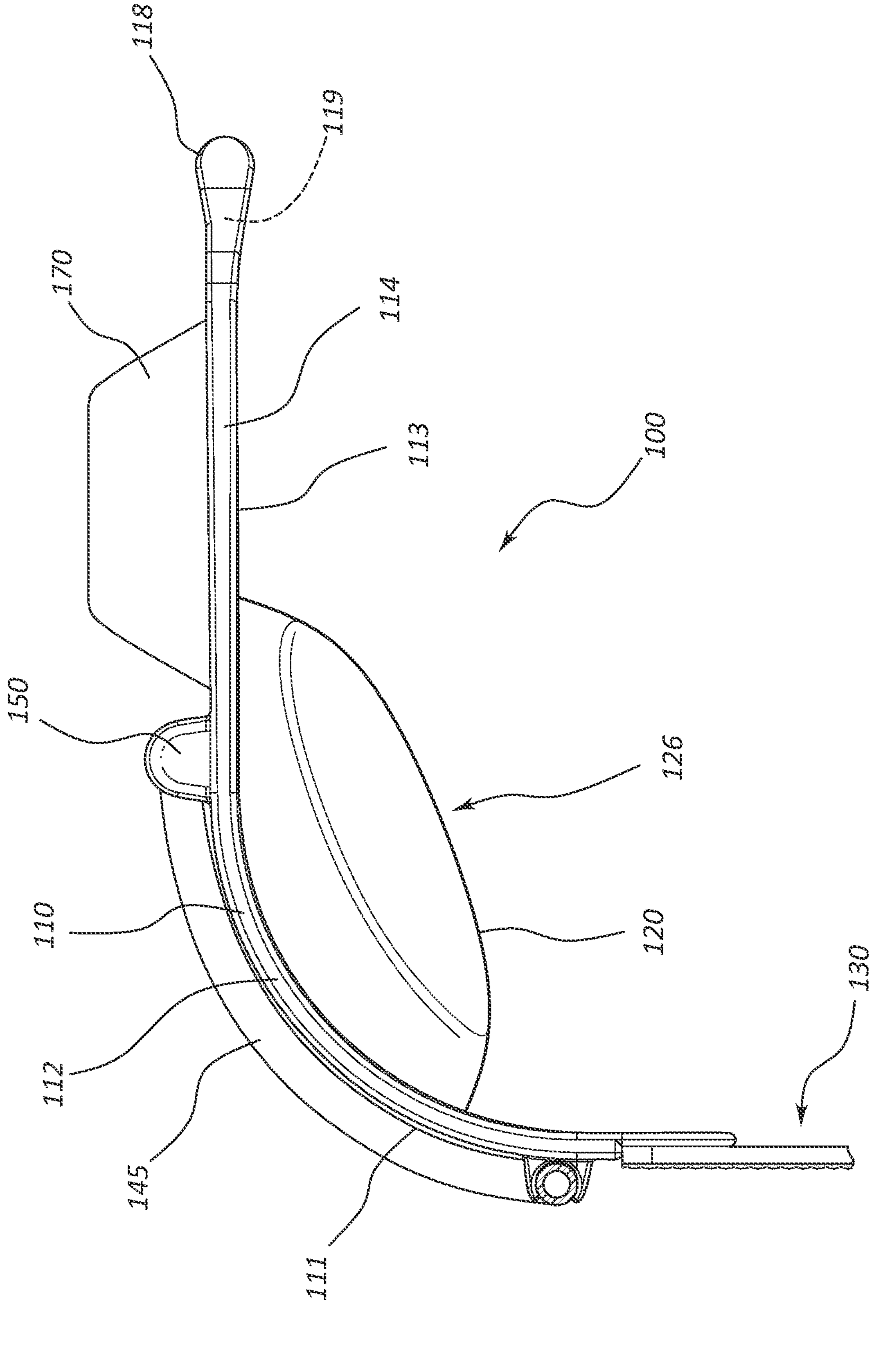
FIG. 4 is a side view of a portion of the radial artery compression device of FIGS. 1-3B with the inflatable chamber in a fully inflated state.

FIGS. 1-4 provide alternative views of a radial artery compression device 100. More particularly, FIG. 1 depicts a radial artery compression device 100 secured to the wrist of a patient 50. FIG. 2 provides a perspective view of an underside of the radial artery compression device 100. FIG. 3A provides a side view of the radial artery compression device 100. FIG. 3B provides a front view of the radial artery compression device 100 showing a front view of the wristband 130. FIG. 4 provides a side view of the radial artery compression device 100 with an inflatable chamber 126 in an inflated state.

As shown in FIGS. 1-4, the radial artery compression device 100 may include a substantially rigid frame 110, a flexible sheet 120, and a wristband 130.

The substantially rigid frame 110 may include an outer surface 111 and an inner surface 113. In some embodiments, the substantially rigid frame 110 is contoured to curve around a thumb-side portion of the wrist 54 of the patient 50. For example, in some embodiments, the substantially rigid frame 110 includes a curved portion 112 (see FIGS. 3A and 4). In the embodiment shown in FIGS. 1-4, the frame 110 is shaped as a curved (e.g., arched) member. The outer surface 111 of the frame 110 (or a portion thereof) may be convex, while the inner surface 113 of the frame 110 (or a portion thereof) may be concave. In some embodiments, the substantially rigid frame 110 further includes a substantially straight portion 114 opposite the curved portion 112, the straight portion 114 configured to be disposed adjacent an underside (i.e., a palmar side) of the wrist 54 of the patient 50. In some embodiments, the substantially rigid frame 110 (or a portion thereof) is transparent. Other shapes and designs of frames, including those configured to match the contours of other parts of the body, are within the scope of this disclosure.

In some embodiments, the curved portion 112 may have a radius of curvature (r) of between 1.5 cm and 2.5 cm (see FIG. 3A). Additionally or alternatively, the degree measure (θ) of an arc formed by the curved portion 112 may be between 45 and 100 degrees. For example, in some embodiments, the curved portion 112 is between 80 and 95 degrees (e.g., approximately 90 degrees).

The flexible sheet 120 may be coupled to the frame 110. For example, in some embodiments, the flexible sheet 120 includes a peripheral portion 122 that is attached to the frame 110 and a central portion that is not attached to the frame 110. In some embodiments, the peripheral portion 122 of the flexible sheet 120 is attached to the frame 110 via welding or an adhesive. The flexible sheet 120 may be made from any suitable material, such as polyurethane or PVC. In some embodiments, the material of the flexible sheet is stretchable. In the depicted embodiment, the flexible sheet 120 is substantially rectangular in shape, although other shapes are also within the scope of this disclosure. In some embodiments, the flexible sheet 120 (or a portion thereof) is transparent. For example, in some embodiments, both the substantially rigid frame 110 (or a portion thereof) and the flexible sheet 120 (or a portion thereof) are transparent, thereby allowing a practitioner to view a radial access site through the frame 110 and the flexible sheet 120. In some embodiments, the practitioner may need to view through only two layers (e.g., the frame 110 and the flexible sheet 120) to view the radial access site. Viewing through only two layers may provide improved visual clarity relative to embodiments in which the radial access site is viewed through more than two layers or parts. Embodiments wherein a flexible sheet or bladder completely surrounds and defines an inflation volume and the bladder is coupled to a frame are also within the scope of this disclosure.

The substantially rigid frame 110 and the flexible sheet 120 may form the inflatable chamber 126. For example, the inner surface 113 of the frame 110 and the flexible sheet 120 may at least partially define the inflatable chamber 126. Stated differently, a wall of the inflatable chamber 126 may be defined by the frame 110. In this fashion, the inflatable chamber 126 may be defined by both a first portion (e.g., the substantially rigid frame 110) of the radial artery compression device 100 that does not change size or shape as the inflatable chamber 126 is inflated and a second portion (e.g., the flexible sheet 120) of the radial artery compression device 100 that does change in size or shape as the inflatable chamber 126 is inflated.

In some embodiments, the radial artery compression device 100 includes a single inflatable chamber 126. Such embodiments may be configured for as ease of construction and/or ease of use. Embodiments with multiple chambers and embodiments wherein a single chamber has multiple lobes or portions configured to provide compression at multiple points on the body are within the scope of this disclosure.

In some embodiments, such as the illustrated embodiment with inflation chamber 126, the maximum capacity of the inflatable chamber may be between 3 mL and 30 mL. For example, in some embodiments, the maximum capacity of the inflatable chamber 126 is between 3 mL and 12 mL, between 3 mL and 20 mL, between 3 mL and 25 mL, between 5 mL and 15 mL, between 10 mL and 20 mL, between 10 mL and 30 mL, or between 15 mL and 30 mL. The inflatable chamber 126 may be configured to apply varying amounts of pressure to a radial access site of the patient 50. In some embodiments, the inflatable chamber 126 provides pressure to the radial access site in a manner that avoids restricting the ulnar artery.

In some embodiments, the radial artery compression device 100 includes tubing 145 that extends from a first aperture 116 (see FIGS. 5A-5E) in the substantially rigid frame 110 to a valve 140. The tubing 145 and the valve 140 may be in fluid communication with the inflatable chamber 126 that is formed by the substantially rigid frame 110 and the flexible sheet 120. In some embodiments, the valve 140 is configured to open and allow fluid to flow through the valve 140 upon coupling (i.e., as a result of coupling) to an inflation device (e.g., a syringe), but closes and prevents fluid flow through the valve 140 upon decoupling, i.e., as a result of decoupling or being detached from the inflation device. In other words, attaching the inflation device to the valve 140 may open the valve 140 and detaching the inflation device from the valve 140 may close the valve 140. As such, the valve 140 may maintain a positive fluid pressure within the inflatable chamber 126 after the inflation device has been decoupled from the valve 140.

In the depicted embodiment, the tubing 145 is coupled to the frame 110 via a connector 150 that protrudes from the outer surface 111 of the frame 110. In some embodiments, the tubing 145 extends from the connector 150 for a length of 5 cm to 15 cm, 6 cm to 15 cm, 8 cm to 15 cm, 10 cm to 15 cm, 12 cm to 15 cm, 6 cm to 12 cm, 6 cm to 10 cm, 6 cm to 8 cm, or 8 cm to 10 cm in length. In other words, in some embodiments, the tubing 145 is between about 5 cm to about 15 cm. In other embodiments, the tubing 145 is of some other length. In still other embodiments, the valve 140 may be directly coupled to the connector 150 such that no tubing 145 is used.

In some embodiments, the radial artery compression device 100 may further include a retainer 160 (e.g., a clip) that is configured to secure a free end of the tubing 145 to the frame 110. In some embodiments, when the radial artery compression device 100 is secured to the right arm of the patient 50, the retainer 160 may be positioned (1) ulnar or radial of the connector 150 and/or (2) proximal or distal (along the length of the arm of the patient) of the connector 150. For example, when the depicted embodiment is secured to the right arm of the patient 50 as shown in FIG. 1, the retainer 160 is positioned radial of and distal of the connector 150. The retainer 160 and the connector 150 may be positioned at a distance from one another such that, when a portion of the tubing 145 adjacent the free end is attached to the retainer 160, only a small length of the tubing 145 protrudes from the radial artery compression device 100, thereby minimizing the bulk of the radial artery compression device 100.

In the illustrated embodiment, a bar 118 is disposed along a second perimeter side of the frame 110 opposite the first perimeter side. The bar 118 is coupled to the frame 110 at each end of the bar 118. The bar 118 is spaced away from the frame 110 to define an elongate slot 119. The length of the elongate slot 119 may be sized to accommodate a width of the wristband 130 and the width of the elongate slot 119 may be sized to accommodate a thickness of the wristband 130. As such, the wristband 130 may pass through the elongate slot 119 and wrap around the bar 118. In some embodiments, the bar 118 may be configured to minimize friction with the wristband 130 and thereby minimize sliding resistance. More specifically, the circumference of the bar 118 may comprise a smooth surface to minimize friction. In other embodiments, the bar 118 may be configured to enhance friction with the wristband 130 and thereby define sliding resistance. More specifically, the circumference of the bar 118 may comprise a rough surface, a sharp edge, or any other suitable feature to resist sliding of the wristband 130. Still in other embodiments, the circumference of the bar 118 may comprise both a smooth portion and a rough portion. As such, the wristband 130 may slide freely on the circumference of the bar 118 when the wristband 130 is pulled in one direction and be inhibited from sliding when the wristband 130 is pulled in a different direction.

As noted above, in the illustrated embodiment, the bar 118 is coupled to the frame 110 such that the elongate slot 119 is closed on all sides. Embodiments wherein the bar 118 is only coupled at one end and the elongate slot 119 is open to a perimeter of the frame 110 are also within the scope of this embodiment. In embodiments wherein the elongate slot 119 is closed, such as the illustrated embodiment, a portion of the wristband 130 maybe threaded though the elongate slot 119 during use. In embodiments wherein the elongate slot 119 is open to a perimeter of the frame 110 (e.g., when only one end of the bar 118 is coupled to the frame 110), a loop or bend in the wristband may be slid over the bar 118 via the open side of the elongate slot 119.

As shown in FIGS. 3A and 3B, the wristband 130 may be coupled to the frame 110 at a fixed end 138 of the wristband 130. The wristband 130 may consist of a single strap that is attached to a first perimeter side of the frame 110. The wristband 130 may be configured to secure the frame 110 on to the wrist 54 of the patient 50. In some embodiments, the entire wristband 130 (or a portion thereof) is opaque. In some embodiments, the wristband 130 is colored and/or decorated. In the illustrated embodiment, the wristband 130 includes a hook and loop fastener system (e.g., Velcro). In some embodiments, the wristband 130 is a single integrated Velcro strap with a single fixed end and a single free end.

In the illustrated embodiment, the wristband 130 includes the fastener system which may be a hook and loop fastener system (e.g., Velcro). The wristband 130 includes an inner surface 131 which may extend from the inner surface 113 of the frame 110, an outer surface 132 which may extend from the outer surface 111 of the frame 110, and a free end 133. In the illustrated embodiment, a hook portion 134 and a loop portion 135 of the fastener system are disposed on the outer surface 132 of the wristband 130. In the illustrated embodiment, the hook portion 134 is disposed adjacent the free end 133 and the loop portion 135 is disposed between the hook portion 134 and the fixed end 138 or the frame 110. In some embodiments, the loop portion 135 may extend from the hook portion 134 to the fixed end 138. The hook portion 134 and the loop portion 135 may be located at other positions along the wristband 130 and/or on the inner surface 131 or on both the inner surface 131 and the outer surface 132 of the wristband 130 without deviating from the functionality of the wristband 130 and as such, these and all other potential locations of the hook portion 134 and the loop portion 135 are within the scope of the present disclosure.

The wristband 130 may include different characteristics along its length. For example, in some embodiments, some portions of the wristband 130 may be more flexible than other portions. In some embodiments, the wristband 130 may be stretchable or substantially non-stretchable or some portions of the wristband 130 may be stretchable while other portions may be substantially non-stretchable. In some embodiments, the loop portion 135 may be spaced away from the hook portion 134 such that, in use, the loop portion 135 does not pass through the elongate slot 119. As such, a more flexible portion of the wristband 130 may be positioned or configured to wrap around the bar 118.

In the illustrated embodiment, the wristband 130 may include a semi-rigid portion 137 adjacent the free end 133. The semi-rigid portion 137 may facilitate inserting the free end 133 through the elongate slot 119 when threading the wristband 130 through the elongate slot 119. Additionally or alternatively, the wristband 130 may include a taper or tapered portion 139 at the free end 133 to further facilitate inserting the free end 133 through the elongate slot 119. In some instances, the semi-rigid portion 137 and/or the taper 139 may facilitate the medical practitioner inserting the free end 133 through the elongate slot 119 and/or threading the wristband 130 through the elongate slot 119 with one hand.

The hook portion 134 may be disposed away from the terminal portion of the free end 133 and thereby define a pull tab 136. As such, the pull tab 136 may be void of the hook section 134 and the loop section 135. The pull tab 136 may include ribs, protruding bumps, a rough surface, or any other suitable feature disposed on either or both of the inner surface 131 and the outer surface 132 to enhance grip-ability of the pull tap 136.

FIGS. 5A-5E provide cross-sectional side views of the radial artery compression device 100 on a cross section of the wrist 54 of a patient 50 in different states of attachment and use. The sequence of configurations shown in FIGS. 5A-5E represent an embodiment of sequence of using the compression device 100. During some uses, when the wristband 130 is secured to the wrist 54 of the patient 50, the inflatable chamber 126 may be positioned adjacent to a radial artery 10 of the patient 50.

Figure 5A:
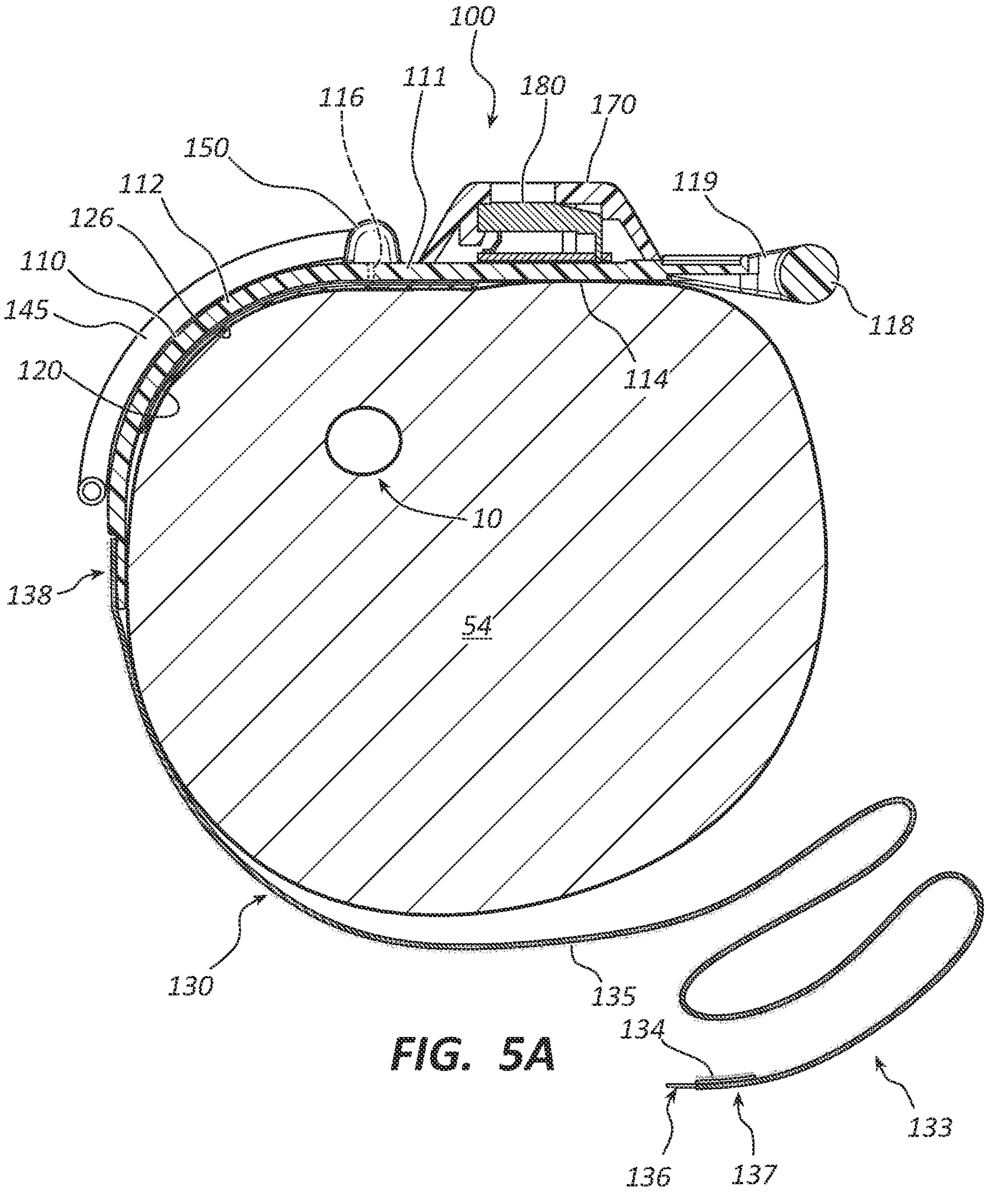
FIG. 5A is a cross-sectional side view of the radial artery compression device of FIGS. 1-4 on the wrist of a patient in a state of initial placement of the radial artery compression device.

Referring to FIG. 5A, the radial artery compression device 100 may be placed or positioned on the wrist 54 of the patient 50 such that the inflatable chamber 126, which may be in an uninflated state, is located over the radial artery 10. In the illustrated embodiment, the curved portion 112 of the frame 110 is placed adjacent the thumb-side portion of the wrist 54 and the straight portion 114 is placed along the underside side portion of the wrist 54. The wristband 130 is shown coupled to the frame 110 at the fixed end 138.

Figure 5B:
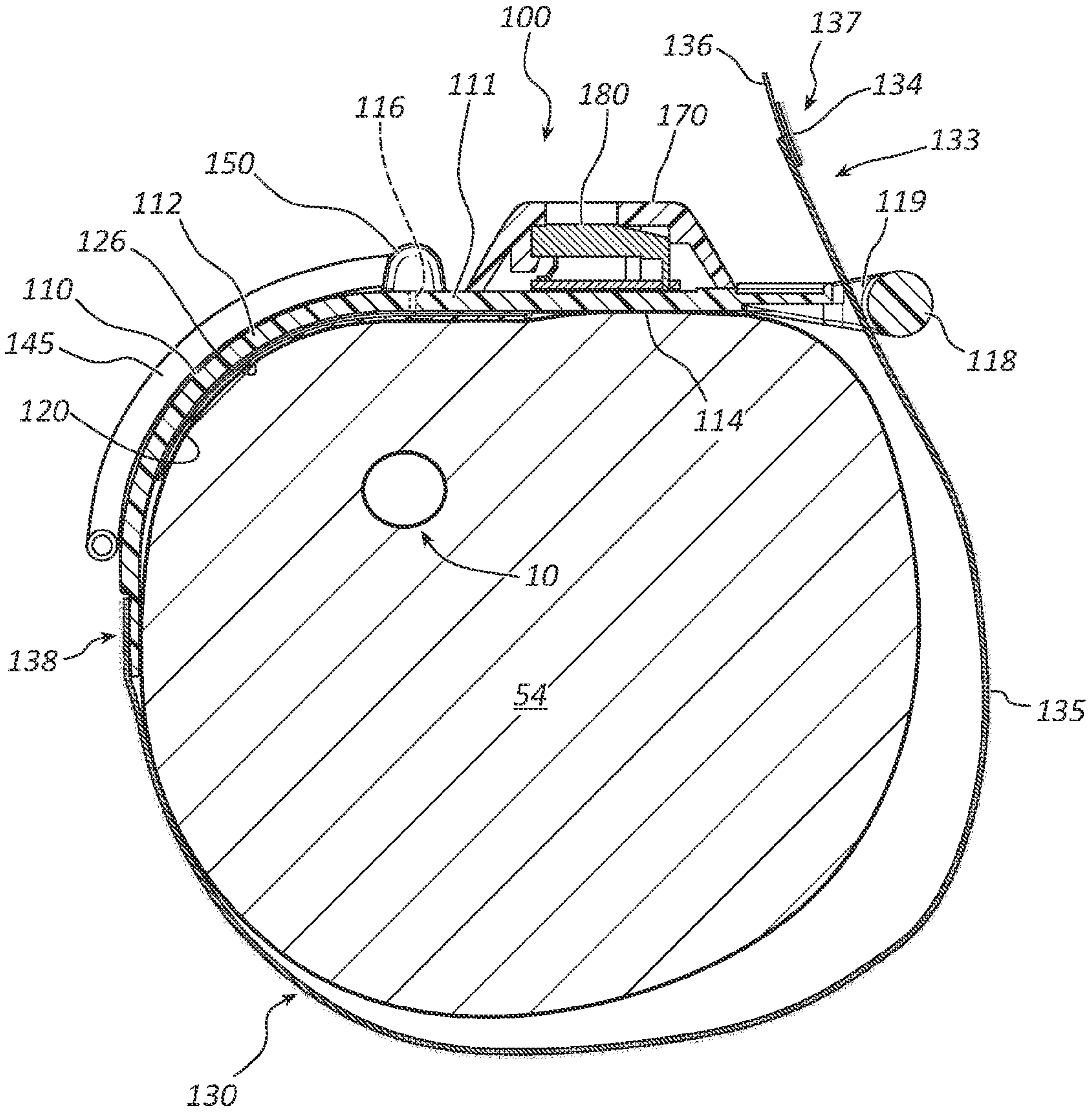
FIG. 5B is a cross-sectional side view of the radial artery compression device of FIGS. 1-4 illustrating the wristband (without tension) wrapped around the wrist and the free end of the wristband inserted through an elongate slot in the frame of the radial artery compression device.

FIG. 5B illustrates the radial artery compression device 100 in a further state of securement to wrist 54. The free end 133 of the wristband 130 is shown inserted or threaded through the elongate slot 119. In use, the medical practitioner may insert the free end 133 into the slot 119 with one hand. The semi-rigid portion 137 of the wristband 130 at the free end 133 may facilitate inserting the free end 133 through the elongate slot 119. At this state of securement, the medical practitioner may re-align or confirm the alignment of the inflatable chamber 126 with the radial artery 10.

Figure 5C:
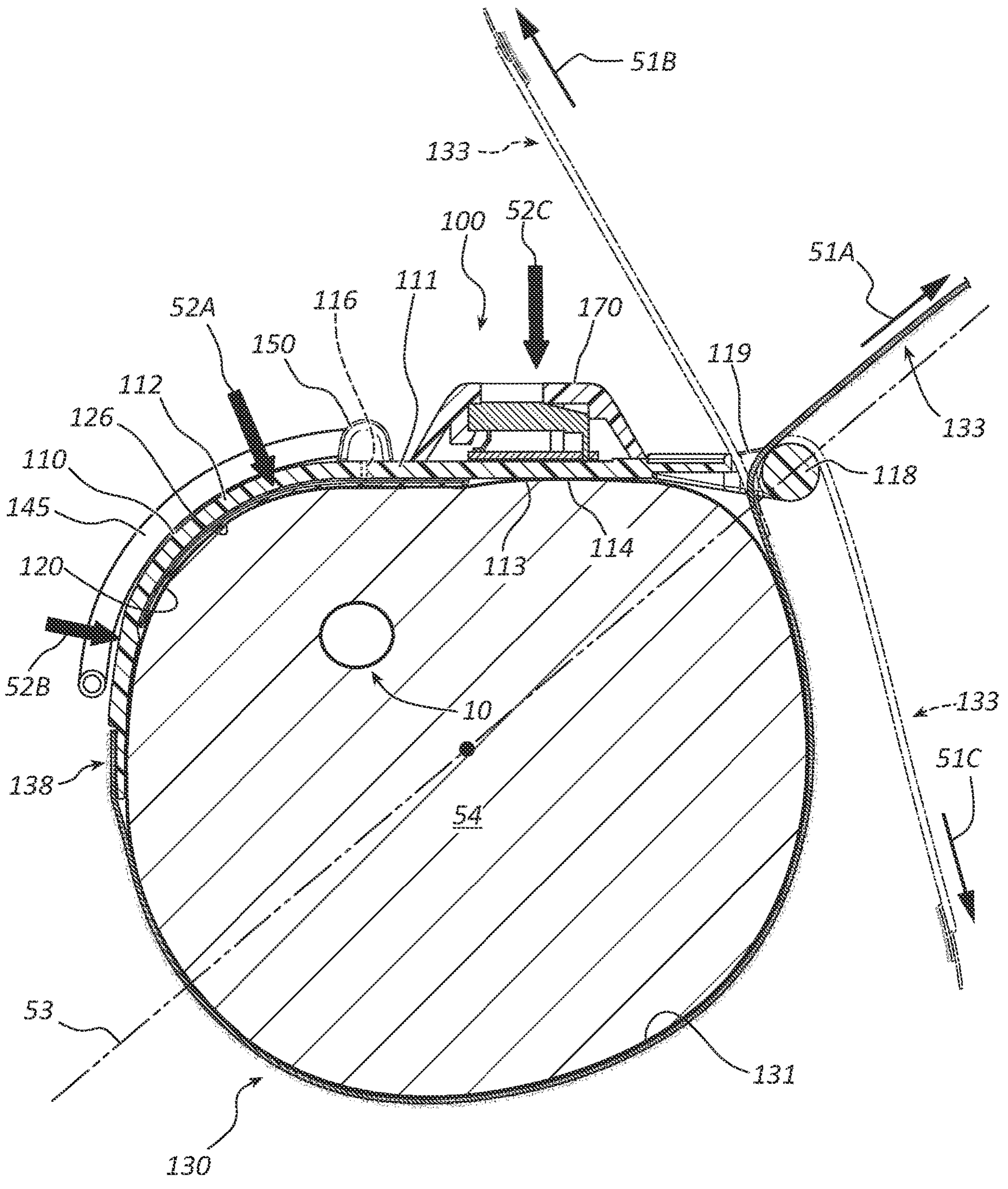
FIG. 5C is a cross-sectional side view of the radial artery compression device of FIGS. 1-4 illustrating the wristband wrapped around the wrist in tension. Also illustrated are different directions in which the wristband may be pulled to create the tension in the wristband.

FIG. 5C illustrates a state wherein tension is being applied to the wristband 130. FIG. 5C shows the wristband 130 tensioned such that the inner surface 131 of the wristband 130 is in contact with the wrist 54. The medical practitioner may apply tension to the wristband 130 by pulling on the free end 133. The medical practitioner may hold or maintain the frame 110 in position of alignment with the radial artery 10 and/or tension the wristband 130 by pulling on the free end 133 only one hand. That is, the compression device 100 may be configured for one-handed tensioning and positioning. For example, application of tension to the free end 133 with one hand may be used to both tension and position the compression device 100. For example, the direction in which tension is applied to the free end 133 may tend to position the compression device 100 as well as tighten the wristband 130. As described below, differences in the direction in which the free end 133 is tensioned may tend to maintain the position of the compression device 100 on the wrist 54 while tensioning the wristband 130, or may tend to rotate or shift the compression device 100 around the wrist 54 during tensioning. In some instances, the tensioning and maintaining or shifting the position of the compression device 100 may be done with only one hand of a practitioner gripping or interacting with the compression device 100.

As shown in FIG. 5C, the free end 133 may be pulled in different directions. In some instances, the free end 133 may be pulled in a neutral direction 51A. The neutral direction 51A may be defined as being perpendicular to the wrist 54 or in a direction leading straight away from a center of the wrist 54. In other words, the neutral direction 51A may be substantially parallel to a line 53 extending through the center of the wrist 54 and the bar 118. Pulling the free end 133 in the neutral direction 51A may increase tension in the wristband 130 such that the frame 110 is drawn closer to the center of the wrist 54 (i.e., increase compression of the frame 110 on the wrist 54) in a neutral or balanced fashion as indicated by the centrally located force 52A. In other words, the curved portion 112 of the frame 110 and the straight portion 114 of the frame 110 may be drawn closer to the center of the wrist 54 in substantially equal amounts. As such, when pulling the free end 133 in the neutral direction 51A, the frame 110 may be drawn closer to the center of the wrist 54 without causing the frame 110 to shift its position or tilt as tension is applied to the wristband 130. As used herein, the neutral direction 51A may define a directional range that may include any direction that is more parallel to the line 53 than perpendicular to the line 53. In other words, a range of angles around the direction shown in FIG. 5C as the neutral direction may tend to tighten the wristband 130 without shifting the position of the compression device 100.

In some instances, the free end 133 may be pulled in a non-neutral direction such as in a first tangential direction 51B. The first tangential direction 51B may be defined as substantially tangent to the wrist 54 and leading away from the outer surface 111 of frame 110. In other words, the free end 133 is disposed above the outer surface 111 of the frame 110 and the free end 133 is pulled away from the outer surface 111. More specifically, the free end 133 is pulled in a direction substantially perpendicular to the line 53 on the frame side of the line 53. Pulling the free end 133 in the first tangential direction 51B may increase tension in the wristband 130 such that the curved portion 112 of the frame 110 is drawn closer to the center of the wrist 54 (i.e., increase compression of the curved portion 112 of frame 110 on the wrist 54) while the straight portion 114 is substantially unaffected by pulling on the free end 133. The straight portion 114 may be substantially unaffected because the wristband 130 may freely slide through the elongate slot 119. In other words, the force 52B adjacent the curved portion 112 may be greater than the force 52C adjacent the straight portion 114. As such, when pulling the free end 133 in the first tangential direction 51B, the frame 110 may shift its position as may be desired by the medical practitioner. In some instances, the position shift may comprise a tilting of the frame 110, i.e., the curved portion 112 may move closer to center of the wrist 54 than the straight portion 114. In other instances, the frame 110 may alternatively, and/or in addition to tilting, slide to a new position along the circumference of the wrist 54, such as rotating the compression device 100 around the circumference of the wrist 54. Pulling the free end 133 in the first tangential direction 51B may be helpful to the medical practitioner in establishing the desired position of the radial artery compression device 100. The first tangential direction 51B may define a directional range which may include any direction that is more perpendicular to the line 53 than parallel to the line 53. In other words, a range of angles around the direction shown in FIG. 5C as the first tangential direction may tend to tighten the wristband 130 while shifting the position of the compression device 100 as described above.

In some instances, the free end 133 may be pulled in a second tangential direction 51C that may be substantially opposite the first tangential direction 51B. The second tangential direction 51C may be defined as tangent to the wrist 54 and leading away from the inner surface 113 of the frame 110. In other words, the free end 133 is disposed below the inner surface 113 of the frame 110, and the free end 133 is pulled away from the inner surface 113. More specifically, the free end 133 is pulled in a direction perpendicular to the line 53 on the non-frame side of the line 53. Pulling the free end 133 in the second tangential direction 51C may increase tension in the wristband 130 such that the straight portion 114 of the frame 110 is drawn closer to the center of the wrist 54 (i.e., increase compression of the straight portion 114 of the frame 110 on the wrist 54) while the curved portion 112 is substantially unaffected by pulling on the free end 133. In this instance, the force 52C is defined by the tension in the wristband 130 as it is wrapped around the bar 118. As such, the force 52C adjacent the straight portion 114 may be defined by up to twice the tension in the wristband 130 while the force 52B adjacent the curved portion 112 may be defined by single tension component in the wristband 130 since it is directly coupled to the frame 110 at the fixed end 138. As such, when pulling the free end 133 in the second tangential direction 51C, the frame 110 may shift its position as may be desired by the medical practitioner. In some instances, the position shift may comprise a tilting of the frame 110 (i.e., the straight portion 114 may move closer to the center of the wrist 54 than the curved portion 112). In other instances, the frame 110 may alternatively, and/or in addition to tilting, slide to a new position along the circumference of the wrist 54, such as rotating around the circumference of the wrist 54. Pulling the free end in the second tangential direction 51C may be helpful to the medical practitioner in establishing the desired position of the radial artery compression device 100. The second tangential direction 51C may define a directional range which may include any direction that is more perpendicular to the line 53 than parallel to the line 53. In other words, a range of angles around the direction shown in FIG. 5C as the second tangential direction may tend to tighten the wristband 130 while shifting the position of the compression device 100 as described above.

Tensioning the wristband 130 in any of the directions 51A, 51B, 51C described above, may thus facilitate tensioning of the wristband 130 and positioning of the compression device 100 using one hand. Stated generally, the free end 133 may be manipulated both to control the position on the compression device 100 on the wrist 54 as well as to tighten the wristband 130 of the compression device 100. In addition to the directional examples 51A, 51B, 51C, described above, a practitioner may also apply tension to the free end 133 proximally or distally along the arm of the patient (in and out of the page in FIG. 5C) to adjust the position of the compression device 100 on the wrist 54. A practitioner may pull on the free end 133 along any angle of a continuous range around the bar 118 extending from the points on either side of the range where the free end 133 would contact the top or side of the wrist 54 (including the directions 51A, 51B, 51C) described above and/or along a continuous range proximally and distally along the patient's arm to tension and position the compression device 100. Again, this manipulation may be done with only one hand of the practitioner interacting with the compression device 100.

Furthermore, displacing the free end 133 in a variety of directions may be configured to tension the wristband 130 around the circumference of the wrist of a patient. For example, interaction between the bar 118 and the wristband 130 may transfer displacement of the free end 133 radially away from the wrist 54 into tension on the wristband 130 around the circumference of the wrist 54. This may facilitate one handed operation and may enable a practitioner to pull the free end 133 in a convenient direction (avoiding, for instance, interference from the patient's anatomy or from other medical equipment) while still providing tension around the circumference of the wrist 54.

Figure 5D:
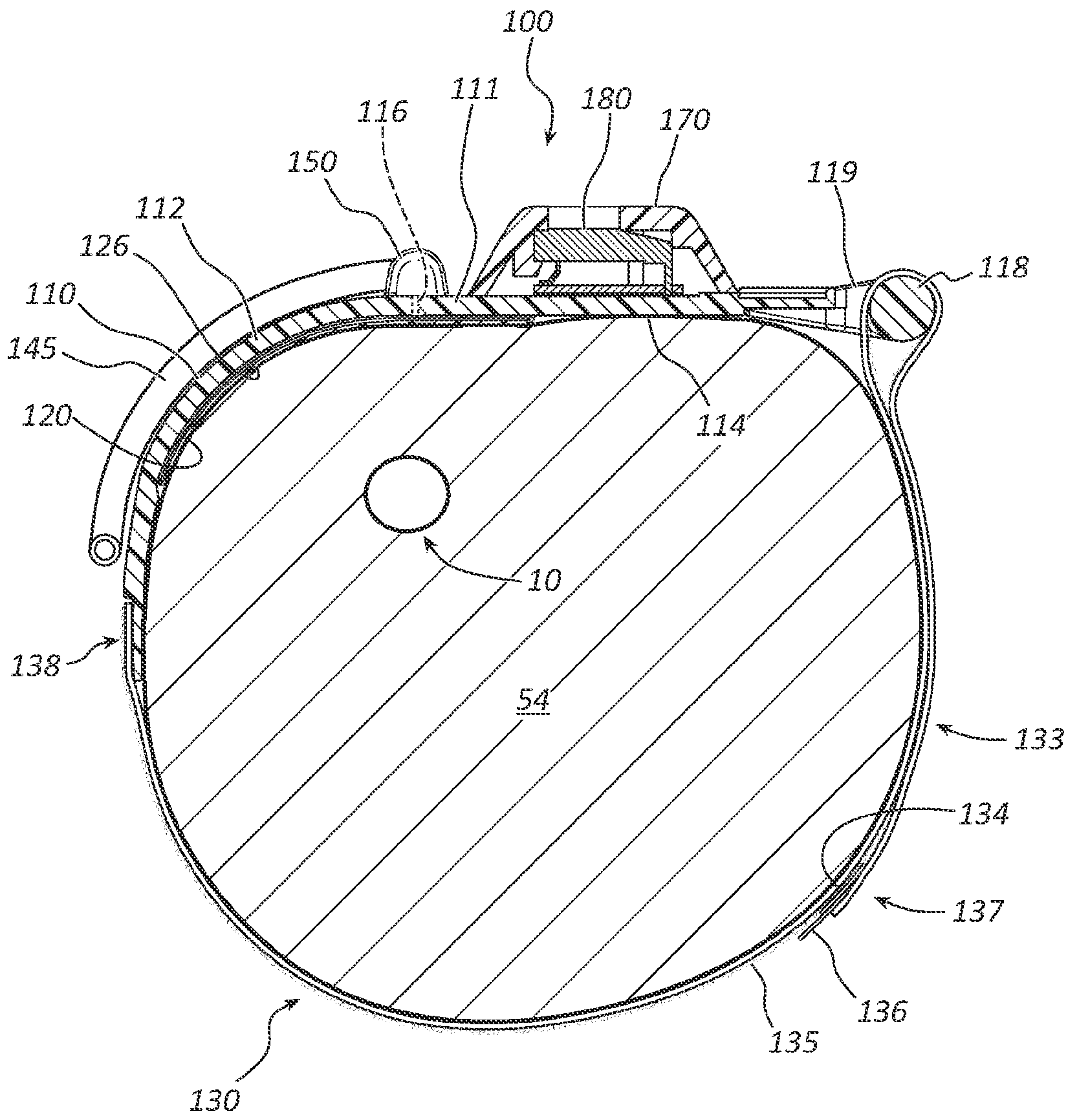
FIG. 5D is a cross-sectional side view of the radial artery compression device of FIGS. 1-4 illustrating the wristband tensioned and the free end secured to the portion of the wristband extending around the wrist.

FIG. 5D illustrates a state where, after the tension in the wristband 130 is established as described above in relation to FIG. 5C, the wristband 130 may be further wrapped around the bar 118 such that the free end 133 is disposed adjacent to and overlaps the portion of the wristband 130 extending around the wrist 54. The free end 133 may then be coupled to the portion of the wristband 130 extending around the wrist 54. In other words, and more specifically, the hook portion 134 disposed adjacent to the free end 133 may be coupled to the loop portion 135. As such, the wristband 130 is configured to facilitate the medical practitioner coupling the free end 133 to the portion of the wristband 130 extending around the wrist 54 with one hand.

Figure 5E:
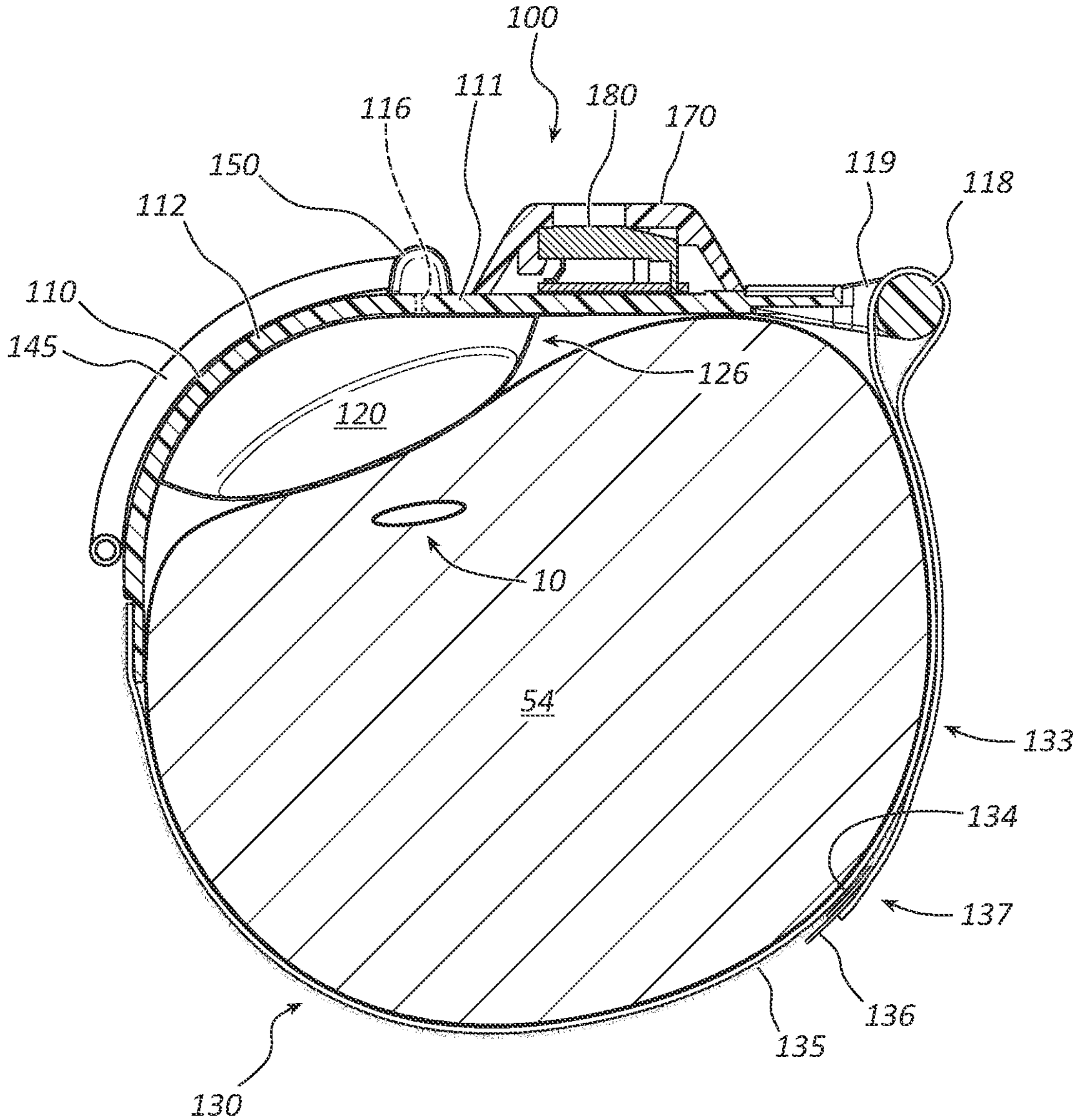
FIG. 5E is a cross-sectional side view of the radial artery compression device of FIGS. 1-4 illustrating the wristband tensioned and secured and the inflatable chamber in an inflated state.

FIG. 5E illustrates a state where, after the radial artery compression device 100 is positioned, the tension in the wristband 130 is established, and the wristband 130 is secured, as described above, the inflatable chamber 126 may be inflated. In some instances, during or after inflation, one or more of the procedures, described above in relation to FIGS. 5A-5D, may be repeated. In some instances, the inflatable chamber 126 may be inflated or partially inflated before or after any one of the processes illustrated in FIGS. 5A-5D. Inflation of the inflatable chamber 126 may be configured to provide and control compression of an arteriotomy site.

In some instances, the medical practitioner may, after completing one or more of the processes described above in relation to FIGS. 5A-5E, adjust the tension in the wristband 130. In such instances, the medical practitioner may, while grasping the free end 133, detach the free end 133 from the portion of the wristband 130 extending around the wrist 54, pull on the free end 133 to increase tension or move the free end 133 toward the bar 118 to reduce tension, and re-attach the free end 133 to the portion of the wristband 130 extending around the wrist 54. Such adjustments may be made with only one hand of the practitioner interacting with the compression device 100.

In some other instances, the medical practitioner may, after completing one or more of the processes described above in relation to FIGS. 5A-5E, adjust the position of the radial artery compression device 100. In such instances, the medical practitioner may, while grasping the free end 133, detach the free end 133 from the portion of the wristband 130 extending around the wrist 54, pull on the free end 133 in a direction configured to adjust the position of the compression device on the wrist 54 (including the examples of such directions recited above), and re-attach the free end 133 to the portion of the wristband 130 extending around the wrist 54. Such adjustments may be made with only one hand of the practitioner interacting with the compression device 100.

Figure 6:
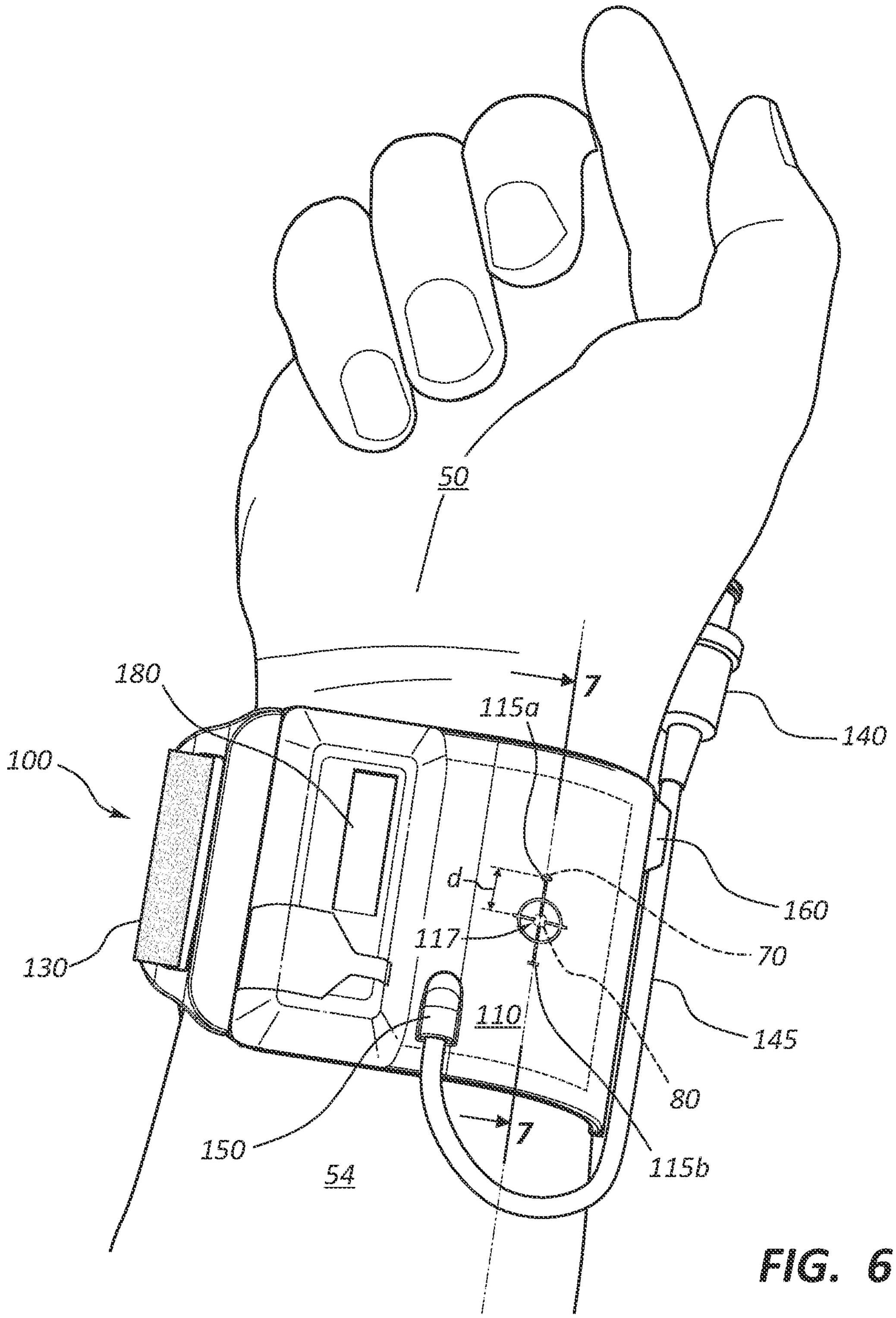
FIG. 6 is a perspective view of the radial artery compression device of FIGS. 1-5E showing the relative positioning of indicia to a puncture site and an arteriotomy site.
Figure 7:
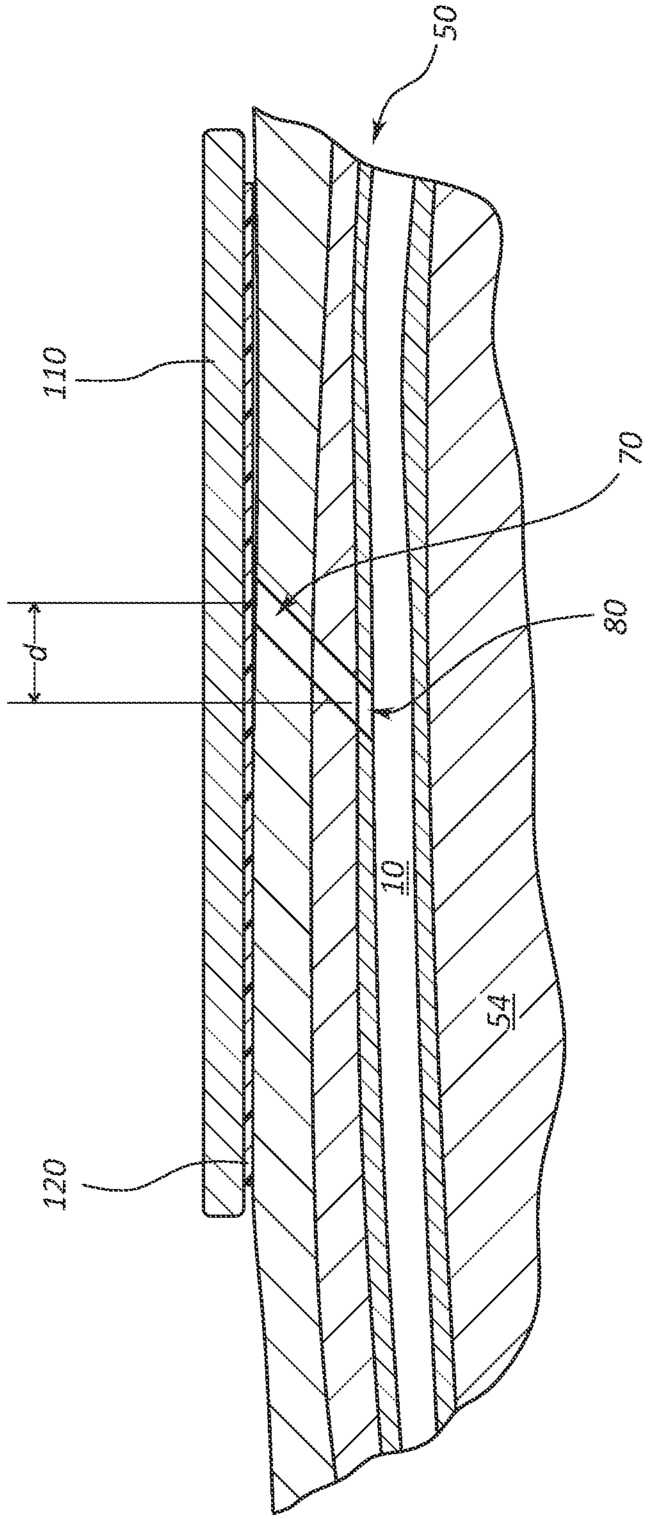
FIG. 7 is a cross-sectional view of the radial artery compression device of FIGS. 1-6 showing a puncture site and an arteriotomy site.

FIGS. 6 and 7 show one embodiment of positioning the radial artery compression device 100 relative to the radial access site, which includes a skin puncture site 70 and an arteriotomy site 80. More particularly, FIG. 6 shows the radial artery compression device 100 secured to the wrist 54 of the patient 50 at a particular location relative to the skin puncture site 70, while FIG. 7 provides a cross-sectional view of the through plane 7-7 of FIG. 6.

When an elongate device, such as a needle, sheath, or catheter, is introduced into the radial artery 10 for an interventional procedure, the elongate device may be inserted at an angle such that the location where the elongate device passes through the skin (i.e., the skin puncture site 70) is not directly above the location where the elongate device passes through the artery wall (i.e., the arteriotomy site 80). In other words, the skin puncture site 70 may be separated from the arteriotomy site 80 by a distance (d). In some embodiments, the distance (d) is from 1-10 mm, including from 2-5 mm, and from 3-4 mm.

In some circumstances, focusing compression on the arteriotomy site 80 rather than the skin puncture site 70 may facilitate hemostasis. In other words, hemostasis may be more rapidly and effectively achieved by applying a compression force to the arteriotomy site 80 in a relatively direct manner. To assist a practitioner in placing the radial artery compression device 100 at a location that provides appropriate compression to the arteriotomy site 80, the radial artery compression device 100 may include indicia on the frame 110. The indicia on the frame 110 may be designed to facilitate identification of the arteriotomy site 80 relative to the visible skin puncture site 70 of the patient 50.

For example, in the depicted embodiment, a first indicium **115*a* is disposed on the frame 110. In the depicted embodiment, the first indicium 115*a* is located at the intersection of a T-shaped mark on the frame 110. When the first indicium 115*a* is aligned with the skin puncture site 70 that is visible through the transparent frame 110 and the transparent flexible sheet 120, a second indicium 117 is disposed directly over the (non-visible) arteriotomy site 80. In the depicted embodiment, the second indicium 117 is the center of a target-shaped mark on the frame 110. In some embodiments, the second indicium 117 is disposed directly above a center of the flexible sheet 120. Stated differently, the second indicium 117 may be disposed directly over a region of the inflatable chamber 126 that is designed to extend furthest from the frame 110 when the inflatable chamber 126 is in an inflated state. In some embodiments, the first indicium 115*a* and the second indicium 117 may be disposed on the flexible sheet 120. In some embodiments, the first indicium 115*a* and the second indicium 117 may be disposed on an inside surface or outside surface of the flexible sheet 120 (i.e., inside or outside of the inflatable chamber 126). Still in other embodiments, the first indicium 115*a* and the second indicium 117 may be disposed on both the frame 110 and the flexible sheet 120**.

In some embodiments, the radial artery compression device 100 may additionally or alternatively include an indicium **115*b*, which may also be disposed on the inside or outside of the flexible sheet 120. The indicium 115*b* may be aligned with a skin puncture site 70 when the radial artery compression device 100 is placed on the left hand of the patient 50. Stated differently, in some embodiments, the radial artery compression device 100 may include indicia to facilitate alignment with the skin puncture site 70 regardless of the arm on which the radial artery compression device 100 is placed. Indicia that differ in some ways from the indicia shown in FIG. 6 may be used for analogous purposes. In other words, various forms of indicia may be used to facilitate proper alignment of the radial artery compression device 100. In some instances, one or more of the procedures described above in relation to FIGS. 5A-5E may be performed and/or repeated during alignment of one or more indicia with the skin puncture site 70**.

In some embodiments, the radial artery compression device 100 may include one or more of the following components: a pressure sensor, a timer, an alarm, a control unit, a power source, a wireless connection, and/or a display 180. In some embodiments, one or more of these components are enclosed within and/or supported by a housing 170. The housing 170 may be fixedly or detachably coupled to the frame 110. For example, in the depicted embodiment, the housing 170 is fixedly coupled to and extends from the frame 110. In embodiments in which the housing 170 is detachably coupled to the frame 110, the housing 170 and/or one or more components disposed therein (e.g., a pressure sensor, a pulse oximeter, a timer, an alarm, a control unit, a power source, a wireless connection, or a display 180) may be reprocessed and/or refurbished for further use.

In some embodiments that include a pressure sensor or pressure transducer (not shown), the pressure sensor may be in fluid communication with the inflatable chamber 126. For example, the pressure sensor may be in fluid communication with the inflatable chamber 126 through a second aperture (not shown) in the substantially rigid frame 110. The pressure within the inflatable chamber 126, as measured by the pressure sensor, may inform protocols for use of the radial artery compression device 100. For example, pressure measurements obtained by the pressure sensor may be relayed to the display 180. The practitioner may use the pressure information on the display 180 to increase or decrease the amount of fluid within the inflatable chamber 126 as desired. In some embodiments, the pressure sensor is detachable from the remaining portions of the radial artery compression device 100. In other embodiments, the pressure transducer is not detachable from the radial artery compression device 100.

As noted above, some radial artery compression devices include a timer. In some embodiments, the timer is a countdown timer. In other or further embodiments, the timer is a stopwatch (i.e., count-up) timer. The timer may be configured to measure time from some reference period, such as when an actuator (e.g., a button or pull tab) is actuated. In some embodiments, time is measured from when the radial artery compression device 100 is positioned on the arm of the patient 50 and initially inflated. The timer may additionally or alternatively measure time from when fluid is initially removed from the inflatable chamber 126 during deflation. In some embodiments, the timer may be configured to measure the amount of time that the inflatable chamber 126 has remained at a particular pressure.

In some instances, the timer may be in communication with the display 180. In some embodiments, the display 180 shows the amount of elapsed time in minutes and seconds. In other or further embodiments, the display 180 may show the amount of elapsed time in hours and minutes. In some embodiments, the display 180 may transition from displaying minutes and seconds to displaying hours and minutes once the amount of elapsed time reaches one hour. In some embodiments, the timer is detachable from the remaining portions of the radial artery compression device 100. In other embodiments, the timer is not detachable.

In some embodiments, the radial artery compression device 100 includes an alarm. In some cases, the alarm may be a visible alarm (e.g., the flashing of light-emitting diodes). In other or further embodiments, the alarm may be audible. The alarm may alert the patient 50 and/or the practitioner to certain information (e.g., the length of time that the radial artery compression device 100 has remained in a particular state). Based on this information, the practitioner and/or the patient 50 may make any needed changes.

In some embodiments, the radial artery compression device 100 may include a wireless connection (e.g., via Bluetooth or Wi-Fi). Information from the radial artery compression device 100 (e.g., information relating to pressure or elapsed time) may be wirelessly transmitted to one of more other devices to alert a medical practitioner of treatment needs, such as the need to modify the amount of pressure provided to the radial artery at a particular time.

The radial artery compression device 100 may be used at or near the conclusion of a medical procedure to facilitate hemostasis of the radial artery 10. In some procedures, the radial artery compression device 100 may be secured to the wrist 54 of the patient 50, such as via the wristband 130. The practitioner may secure the radial artery compression device 100 to the wrist 54 of the patient 50 such that the inflatable chamber 126 of the radial artery compression device 100 is positioned adjacent to a radial access site. For example, in some embodiments, the radial artery compression device 100 is placed on the wrist 54 around a portion of an elongate medical instrument that accesses the radial artery of the patient 50 through a radial access site.

In some circumstances, the practitioner may align the first indicium **115*a* on the frame 110 of the radial artery compression device 100 with the skin puncture site 70 of the patient 50. For example, the practitioner may view the skin puncture site 70 through the frame 110 and the flexible sheet 120 and align the first indicium 115*a* on the frame 110 with the skin puncture site 70. When the first indicium 115*a* is aligned with the skin puncture site 70, the inflatable chamber 126 of the radial artery compression device 100 may be positioned to provide compression to the arteriotomy site 80 that is upstream of the skin puncture site 70. Stated differently, when the first indicium 115*a* of the radial artery compression device 100 is aligned with the skin puncture site 70 of the patient 50, the inflatable chamber 126 may be positioned directly over an arteriotomy site 80 of the patient 50. In some embodiments, the second indicium 117 is disposed directly over the arteriotomy site 80 when the first indicium 115*a* is aligned with the skin puncture site 70**.

Once the radial artery compression device 100 is properly placed on the arm of the patient 50, the inflatable chamber 126 may be inflated in any suitable manner. For example, in some embodiments, the practitioner may connect an inflation device (e.g., a syringe) to the valve 140. Connecting the inflation device to the valve 140 may open the valve 140, allowing the practitioner to deliver fluid into the inflatable chamber 126. For example, a practitioner may advance a plunger of a syringe that is connected to the valve 140, causing fluid to pass through the valve 140, the tubing 145, and the first aperture 116 to enter into the inflatable chamber 126. The delivery of fluid to the inflatable chamber 126 may cause the inflatable chamber 126 to expand, thereby increasing the amount of pressure that is applied to the radial access site. Stated differently, inflating the inflatable chamber 126 may increase pressure that is applied to the radial access site.

In some circumstances, the inflatable chamber 126 may first be partially inflated to provide some compression force to the radial access site. With the inflatable chamber 126 in a partially inflated state, an elongate medical device that is partially inserted into the radial artery 10 may be withdrawn from the radial artery 10 such that no medical device extends through the skin puncture site 70 of the patient 50 to the arteriotomy site 80.

After the elongate medical device has been removed, fluid may then be delivered to the inflatable chamber 126 in an amount that is sufficient to stop bleeding at the arteriotomy site 80. For example, in some embodiments, sufficient fluid may be provided to inflate the inflatable chamber 126. Once enough fluid has been delivered to the inflatable chamber 126 to stop the bleeding, fluid within the inflatable chamber 126 may be slowly withdrawn until a flash of blood is visible at the skin puncture site 70 through the frame 110 and the flexible sheet 120. At this stage, additional fluid (e.g., 1-2 mL) may be injected back into the inflatable chamber 126 to stop the bleeding. This process may provide adequate pressure to achieve hemostasis while maintaining patency of the radial artery 10. In other words, this protocol can be used to ensure that sufficient pressure is provided to prevent bleeding, while avoiding the application of excessive force (which can unduly restrict blood flow through the radial artery 10).

As the arteriotomy site 80 and/or the skin puncture site 70 begin to heal, the amount of compression needed to maintain hemostasis may decrease. Accordingly, the practitioner may deflate the inflatable chamber 126 over a series of stages. Such deflation may follow a particular predetermined protocol. For example, in some embodiments, after the radial artery compression device 100 has been used to apply a compressive force for some period of time (e.g., 5 minutes to 5 hours), a predetermined volume (e.g., 0.5 mL to 3 mL) of fluid may be removed every 2-3 minutes until all of the air is removed. Provided that the removal of compression force does not result in further bleeding, the radial artery compression device 100 may then be removed from the patient 50. In other words, once compression is no longer needed to ensure hemostasis, the radial artery compression device 100 may be removed from the patient 50.

In some instances, fluid may be removed from the inflatable chamber 126 based on information provided by the radial artery compression device 100. For example, in some embodiments, the inflatable chamber 126 may be deflated based on information obtained from a timer or an alarm of the radial artery compression device 100. For example, the radial artery compression device 100 may count the amount of time that has elapsed since the radial artery compression device 100 was placed on the patient 50 and alert the practitioner of the proper time to begin removing fluid from the inflatable chamber 126. The timer may be activated by an actuator, such as a button or a pull tab. In some embodiments, the timer may count up. In other or further embodiments, the timer may count down. The radial artery compression device 100 may also indicate the timing for staged deflation. In some instances, the practitioner or the patient 50 is alerted to the need to remove fluid based on a visible indicator (e.g., information provided on the display 180). The information from the visible indicator may be provided on the display 180, via lights (e.g., light-emitting diodes), or in some other manner. In other or further embodiments, the practitioner or the patient 50 is alerted to the need to remove fluid based on one or more sounds (e.g., the sounds of an audible alarm) that are emitted from the radial artery compression device 100. In some embodiments, lights (e.g., LEDs) or other indicia inform the practitioner of the stage of deflation. For example, in some embodiments, lights may be used to indicate the number of times fluid has been removed from the inflatable chamber 126.

Figure 8:
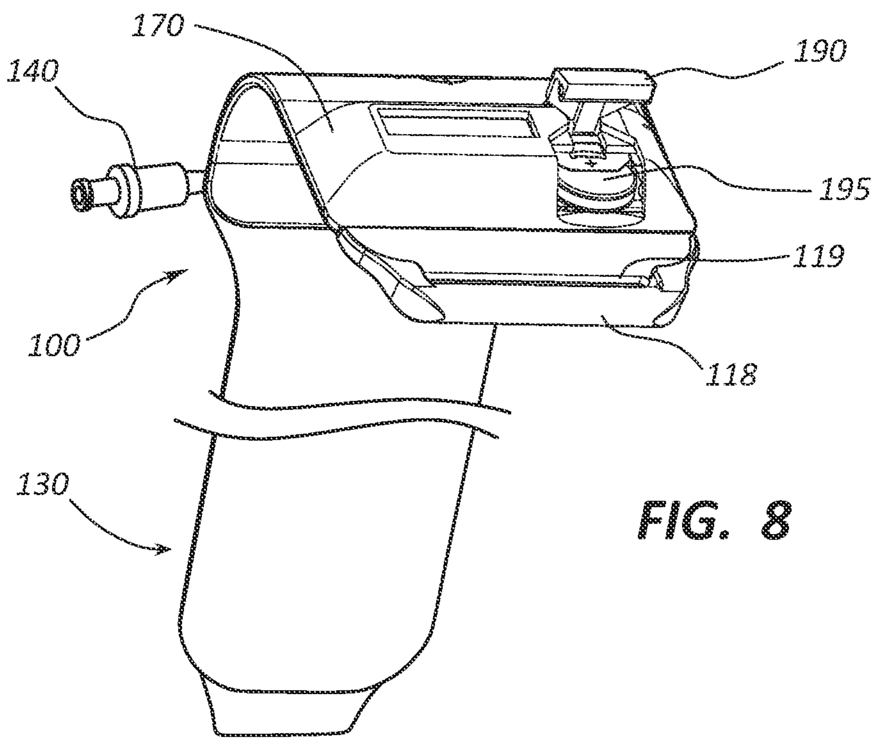
FIG. 8 is a perspective view of the radial artery compression device of FIGS. 1-7 showing a battery removal mechanism.

The radial artery compression device 100 may be powered by any suitable power source. For example, in the embodiment depicted in FIGS. 1-8, the radial artery compression device 100 includes a battery 195 that is disposed within the housing 170. The battery 195 may provide power to a pressure sensor, a timer, an alarm, and/or the display 180. In some embodiments, the radial artery compression device 100 is configured to facilitate removal of the battery 195 from the housing 170. For example, the radial artery compression device 100 may include a battery latch 190 that is rotatably coupled to the housing 170. The battery latch 190 may be opened as shown in FIG. 8 to remove the battery 195 from the radial artery compression device 100. In other words, the radial artery compression device 100 may be configured to facilitate removal of one or more batteries 195 for the housing 170. Facile removal of the battery 195 may allow the radial artery compression device 100 to be discarded separately from battery waste.

Figure 9:
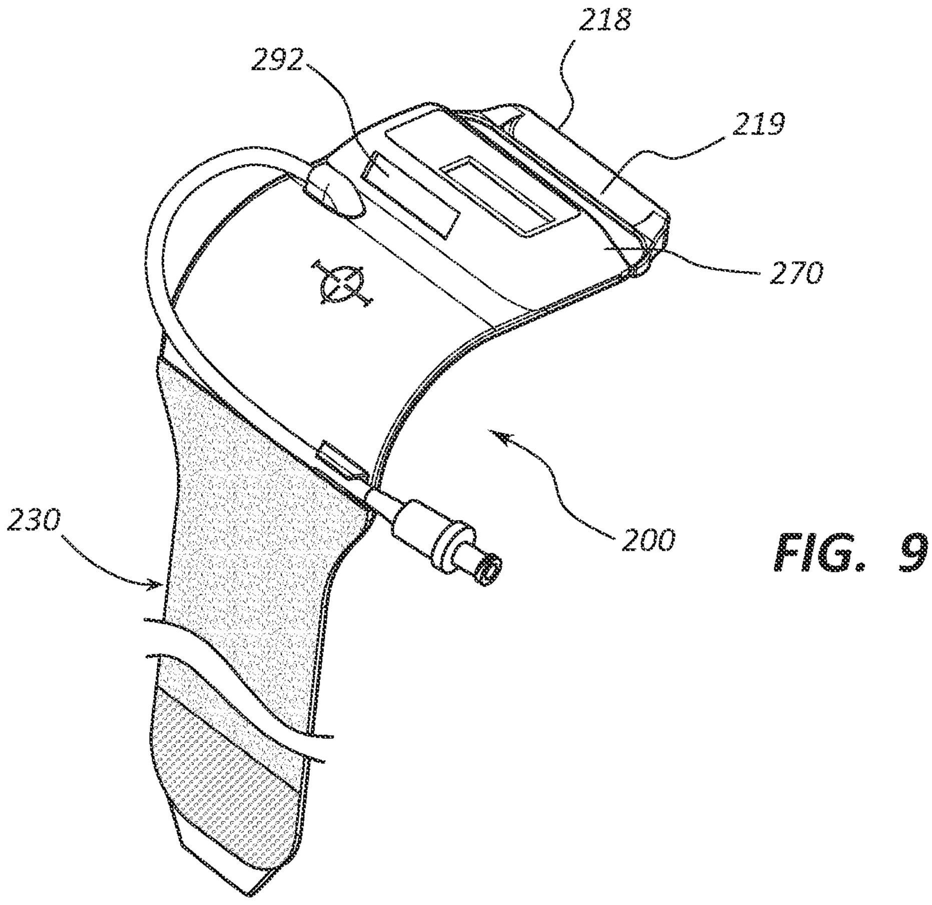
FIG. 9 is a perspective view of an embodiment of a solar-powered radial artery compression device.

Radial artery compression devices need not be powered by one or more batteries. For example, FIG. 9 provides a perspective view of a radial artery compression device 200 that includes a solar panel 292 that is supported by a housing 270. The radial artery compression device 200 may use solar energy to power components such as a pressure sensor, a timer, an alarm, lights, and/or a display. Alternatively, some radial artery compression devices may be powered by a slow-discharge capacitor. The use of a slow-discharge capacitor may allow the radial artery compression device to be discarded without concern for battery waste. In still other embodiments (e.g., embodiments lacking components such as a pressure sensor, a timer, an alarm, lights, and a display), the radial artery compression device 200 may not include a power source within the housing 270.

Figure 10:
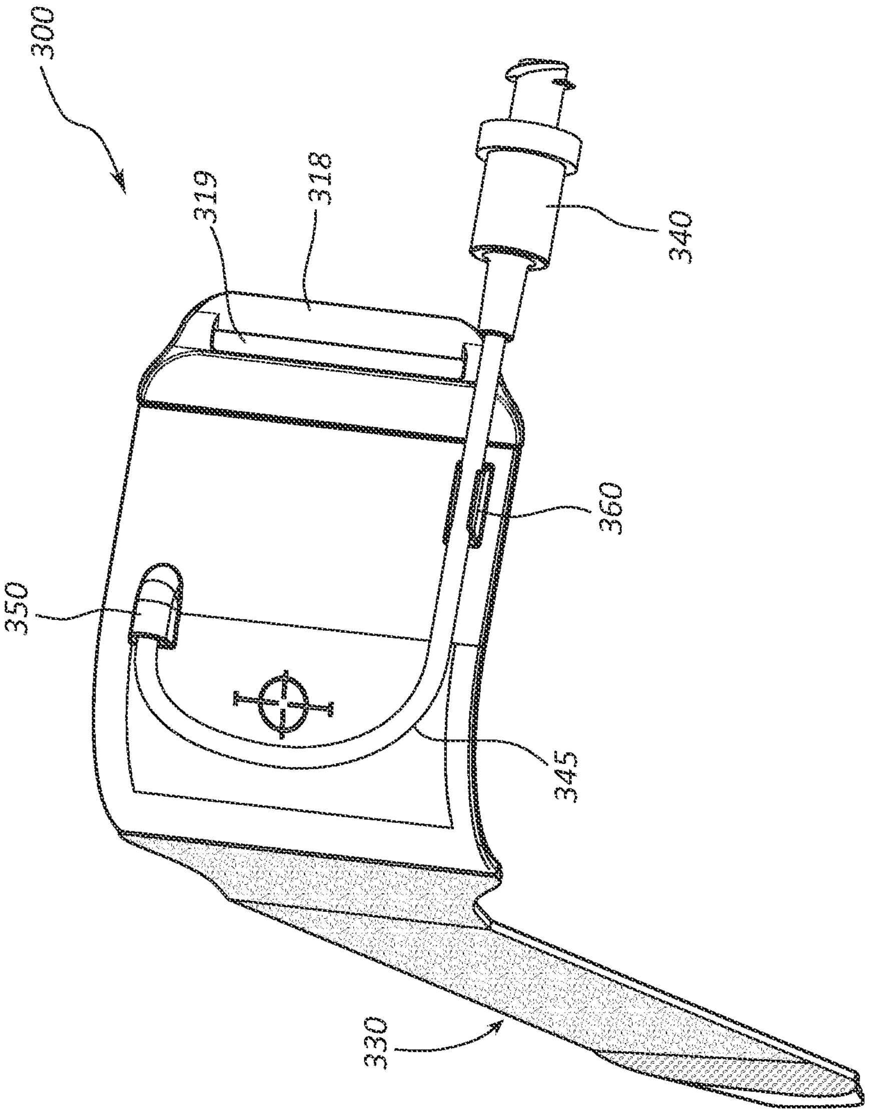
FIG. 10 is a perspective view of another embodiment of a radial artery compression device.

FIG. 10 provides a perspective view of another embodiment of a radial artery compression device 300. The radial artery compression device 300 is generally analogous to the radial artery compression devices 100, 200 described above. Disclosure relating to the embodiments of FIGS. 1-9 may be analogously applied to the embodiment of FIG. 10. As with the embodiment of FIG. 9, elements in FIG. 10 are designated with like references numerals to analogous elements of the embodiment of FIGS. 1-8 and the embodiment of FIG. 9, however the lead digit has been incremented between each embodiment. In the embodiment shown in FIG. 10, the connector 350 and the retainer 360 are positioned in different locations when compared to the connectors and retainers shown in FIGS. 1-9.

When the radial artery compression device 300 is disposed on the right wrist 54 of a patient 50 for placement over a radial artery 10, the connector 350 is both proximal and radial of the retainer 360. Tubing 345 may initially extend radially from the connector 350 and then bend such that a valve 340 at the free end of the tubing 345 is disposed ulnar of the connector 350. The retainer 360 may secure the tubing 345 adjacent to the remaining portions of the radial artery compression device 300.

Figure 11:
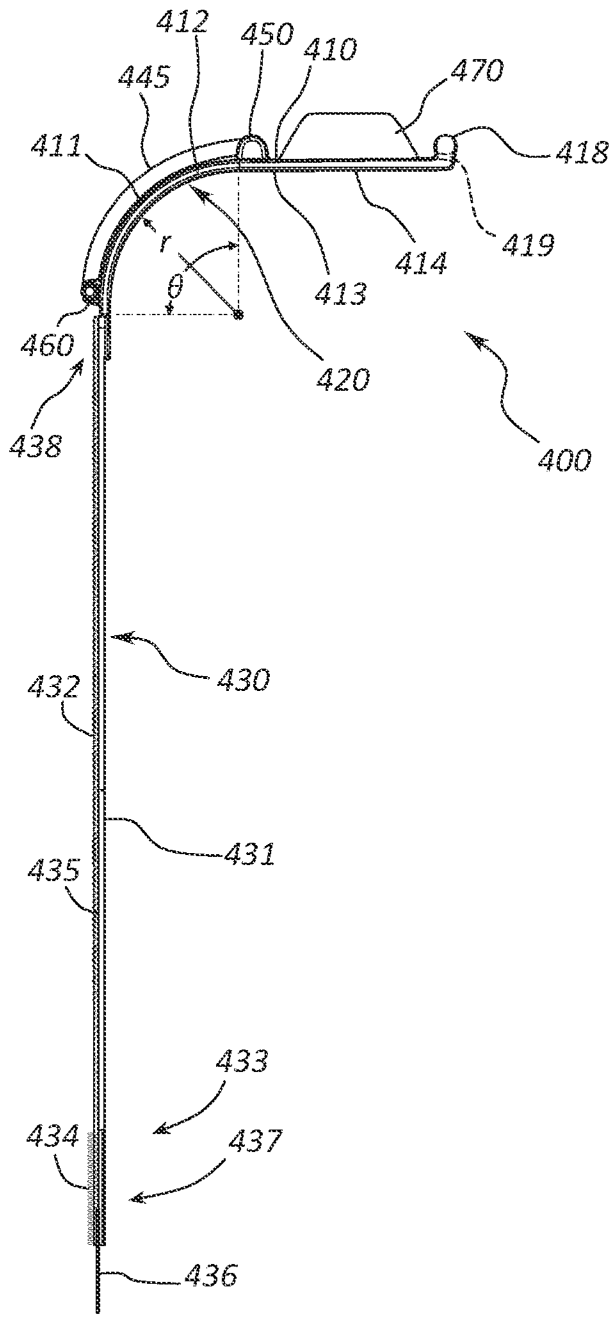
FIG. 11 is a side view of another embodiment of a radial artery compression device.

FIG. 11 provides a side view of another embodiment of a radial artery compression device 400. The radial artery compression device 400 is generally analogous to the radial artery compression devices 100, 200, and 300 described above. Disclosure relating to the embodiments of FIGS. 1-10 may be analogously applied to the embodiment of FIG. 11. As with the preceding embodiments, elements in FIG. 11 are designated with like references numerals to analogous elements of the embodiments of FIGS. 1-10, however the lead digit has been incremented. For example, the bar 418 may in some respects resemble the bar 118 and comprise some of the features described in relation to the bar 118 of FIGS. 1-8. However, in the embodiment shown in FIG. 11, the bar 418 is disposed at different location when compared to the bar 118 as shown in FIGS. 1-8.

As shown in FIG. 11, the bar 418 is coupled to the outer surface 411 of the frame 410. The bar 418 may thus be spaced away from the outer surface 414 of the frame 410 to define the elongate slot 419. As such, when the wristband 430 is inserted through the slot 419, the wristband 430 may extend through the slot 419 in a direction substantially parallel to the straight portion 414 of the frame 410. The parallel direction of the wristband 430 may simplify insertion of the wristband 430 into the slot 419 and may also prevent or inhibit pulling on the patient's skin or pinching of the patient's skin when tension is applied to the wristband 430. In some embodiments, the bar 418 may be disposed inward from the perimeter of the frame 410. In other words, a portion of the frame 410 may extend outward or beyond the bar 418. As such, when the wristband 430 is inserted through the slot 419, the wristband 430 may be disposed above or extend along the outer surface 414 before extending through the slot 419, which may limit or prevent pinching of the patient's skin when tension is applied to the wristband 430.

FIGS. 12-15 illustrate a frame 510 of another embodiment of a radial artery compression device 500. The radial artery compression device 500 is generally analogous to the radial artery compression devices 100, 200, 300, and 400 described above. Disclosure relating to the embodiments of FIGS. 1-11 may be analogously applied to the embodiment of FIGS. 12-15. As with the preceding embodiments, elements in FIGS. 12-15 are designated with like reference numerals to analogous elements of the embodiments of FIGS. 1-11; however, the lead digit has been incremented. For example, the frame 510 may in some respects resemble the frame 110 and comprise some of the features described in relation to the frame 110 of FIGS. 1-8.

Figure 12:
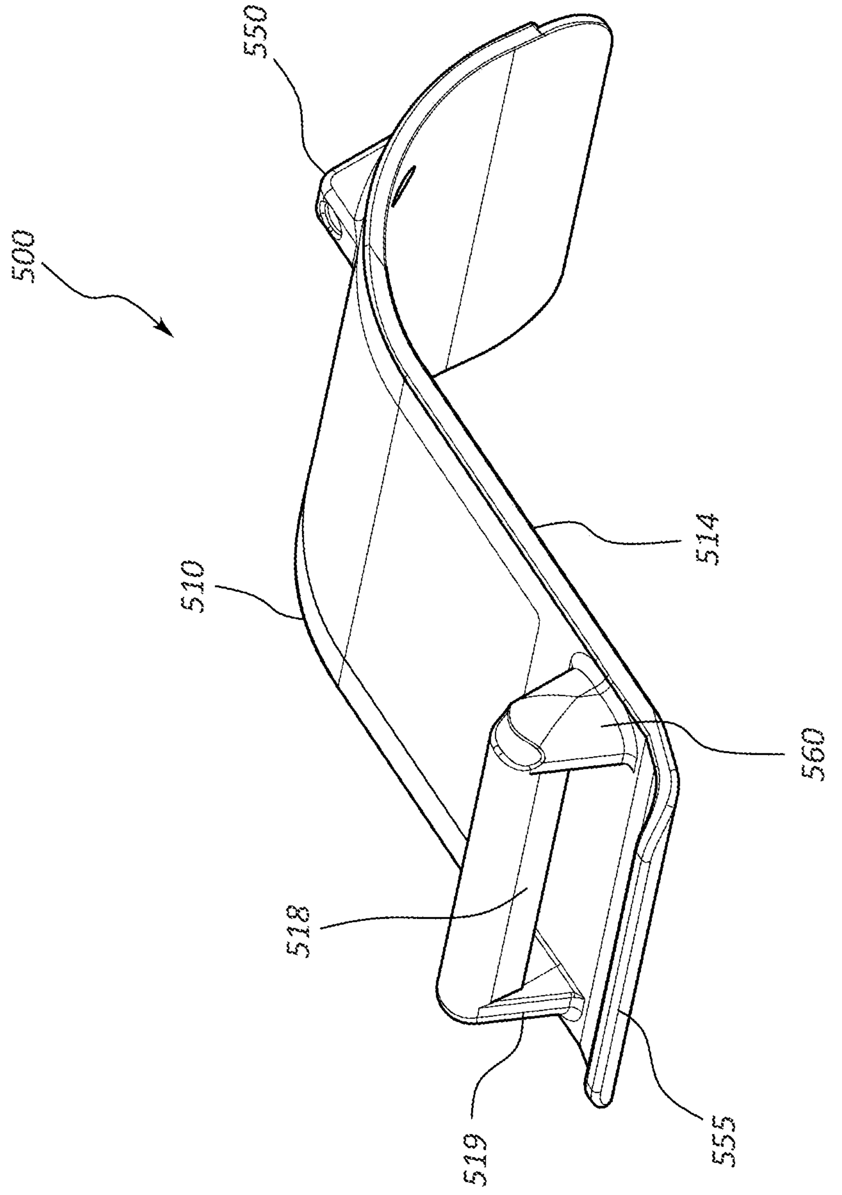
FIG. 12 is a perspective view of a frame of another embodiment of a radial artery compression device.
Figure 13:
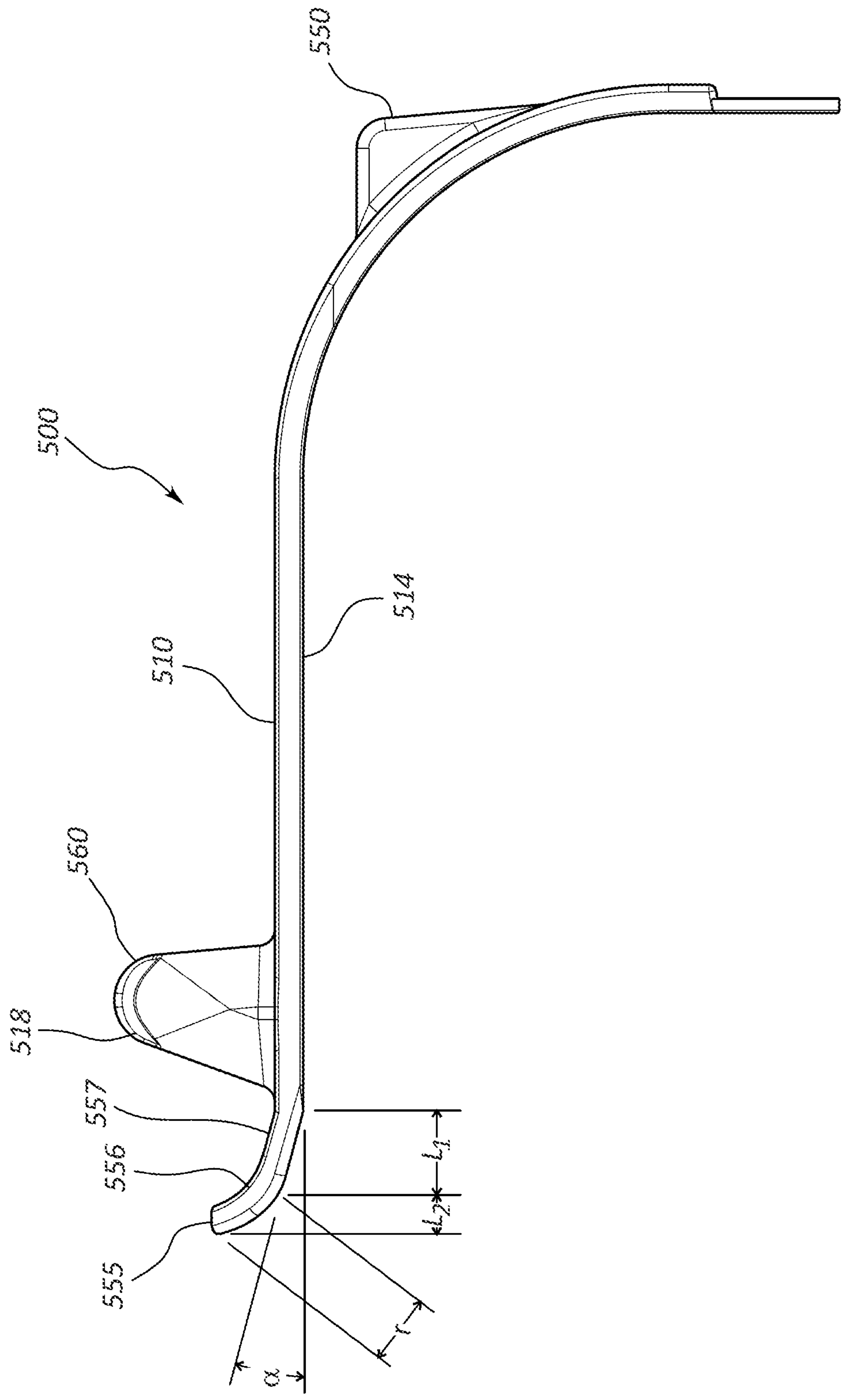
FIG. 13 is a side view of the frame of FIG. 12.

As shown in FIGS. 12 and 13, a bar 518 is coupled to the frame 510. The bar 518 is spaced away from an upper surface of the frame 510 to define an elongate slot 519. The bar 518 may include a retainer 560 configured to receive and retain a tubing coupled to a connector 550. An extension portion 555 of the frame 510 extends beyond the bar 518 such that the bar 518 is positioned away from an end perimeter of the frame 510. In some embodiments, the extension portion 555 is formed as an integral portion of the frame 510. In other embodiments, the extension portion 555 is formed of a flexible material different than the material of the frame 510. For example, the flexible material may be a fabric of natural or polymeric fibers or a polymeric film. Other flexible materials are contemplated.

As illustrated, the extension portion 555 includes a curved segment 556 and a straight, angled segment 557 disposed between the curved segment 556 and the bar 518 such that a free end of the extension portion 555 is elevated above a plane extending from a straight portion 514 of the frame 510. In other embodiments, the extension portion 555 may be configured with only an angled straight segment or only a curved segment. The curved segment 556 includes an outside radius r ranging from about zero millimeters to about 15 millimeters and may be about six millimeters and a length $L_2$ ranging from about zero millimeters to about 13 millimeters and may be about six millimeters. The angled segment 557 includes an angle α relative to the plane extending from the straight portion 514 ranging from zero degrees to about 45 degrees and may be about 15 degrees and a length $L_1$ ranging from about zero millimeters to about 13 millimeters and may be about two millimeters.

Figure 14:
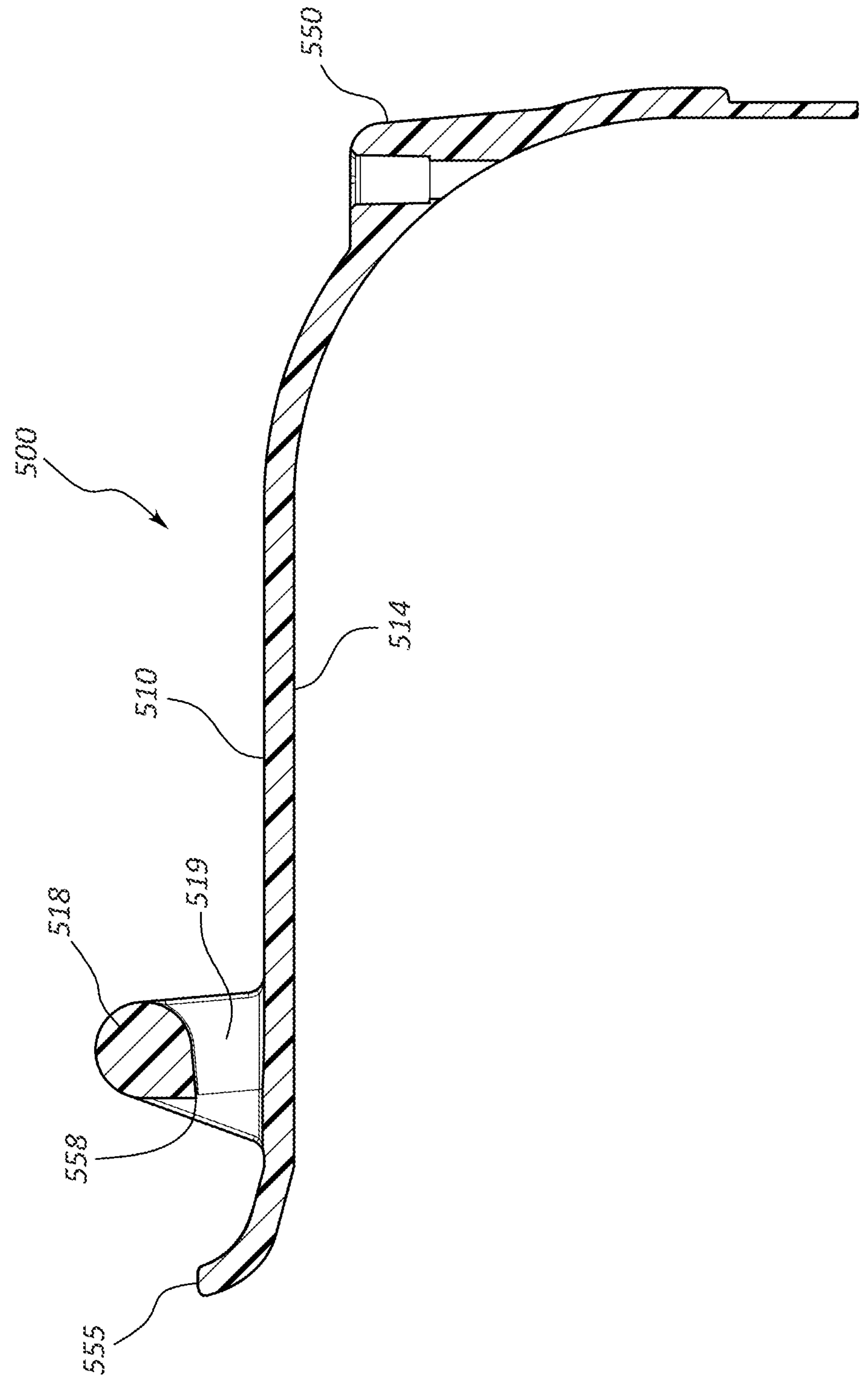
FIG. 14 is a cross-sectional side view of the frame of FIG. 12.

As depicted in FIG. 14, the extension portion 555 includes a biting edge 558 disposed at the free end of the extension portion 555. In the depicted embodiment, the biting edge 558 includes a full radius. In another embodiment, the biting edge 558 may include a straight edge oriented transverse to a longitudinal axis of the frame 510. In other embodiments, the biting edge 558 may include serrated teeth disposed along a length of the biting edge 558. Other embodiments of the biting edge 558 are contemplated.

Figure 15:
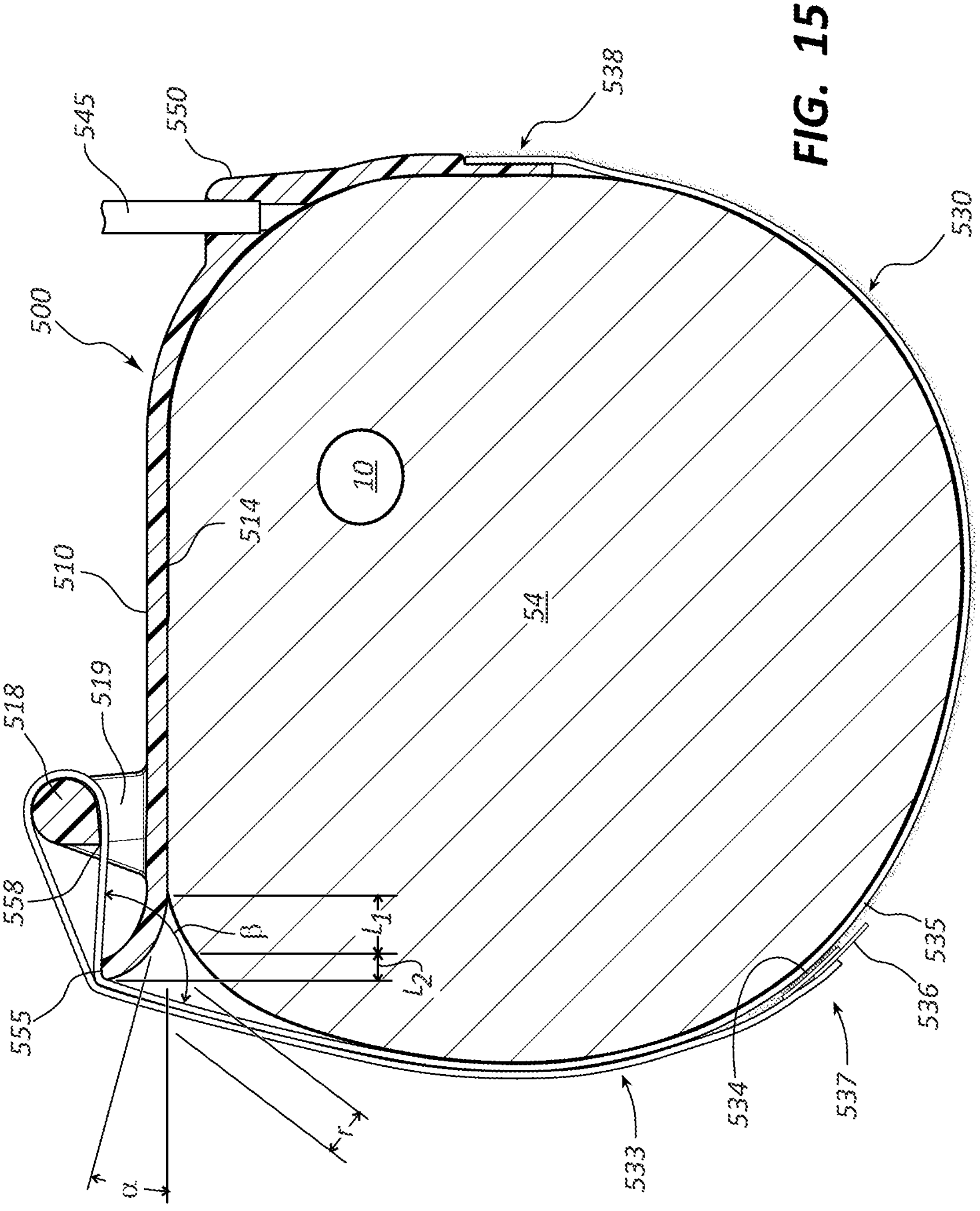
FIG. 15 is a cross-sectional view of the radial artery compression device of FIGS. 11-14 illustrating a wristband tensioned and a free end secured to a portion of the wristband extending around a wrist.

When the radial artery compression device 500 is applied to the wrist 54 of a patient to provide hemostasis to the radial artery 10, a wristband 530 is wrapped around the wrist 54, inserted through the slot 519, and at least partially wrapped around the bar 518, as shown in FIG. 15. The wristband 530 may extend over the extension portion 555 and through the slot 519 to form an angle β. A working range of angle β can be from about 45 degrees to about 180 degrees and may be about 100 degrees. Angle β may be adjusted by adjusting dimensions of the outer radius r, length L1, length L2, a height of the bar 518 above the frame 510, or any combination thereof. For example, when L2 is relatively long, angle β may be relatively low and when L2 is relatively short, angle β may be relatively high. When angle β is within the working range, a cinch force of the wristband 530 applied normally against the biting edge 558 is relatively high. This configuration can result in the radial artery compression device 500 providing adequate hemostatic compressive force to the artery 10 without overtightening of the wristband 530 and pinching of the patient's skin between the wristband 530 and the frame 510. When the angle β is higher than the working range, the cinch force to secure the wristband 530 against the biting edge 558 is relatively low resulting in overtightening of the wristband 530 and pinching of the patient's skin between the wristband 530 and the frame 110 to achieve an adequate hemostatic compressive force to the artery 10.

Some radial artery compression devices described herein, such as radial artery compression devices 100, 200, 300, 400, and 500 may be placed on either arm of the patient 50. For example, while the radial artery compression device 100 is shown in FIG. 1 on the right arm of the patient 50, the radial artery compression device 100 may alternatively be used on the left arm of the patient 50. When the radial artery compression device 100 is disposed on the left arm of the patient 50, the frame 110 may be contoured to curve around a thumb-side portion of the left wrist 54 of the patient 50. Stated differently, when the radial artery compression device 100 of FIG. 1 is properly placed on the left arm of the patient 50, the radial artery compression device 100 of FIGS. 1-8 may be rotated such that the connector 150 is both ulnar of and distal of the retainer 160.

While the compression devices described above are described as radial artery compression devices, some compression devices may, additionally or alternatively, be suitable for compression of an ulnar artery. For example, a compression device may be placed on the patient such that the frame curves around the ulnar side of the wrist. When placed on the patient in this manner, the inflatable chamber may be positioned adjacent to the ulnar artery such that inflation of the inflatable chamber applies pressure to an access site in the ulnar artery. Thus, some compression devices described herein may be used to promote healing at access sites in an ulnar artery.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A radial artery compression device, comprising:

a frame, the frame comprising:

an outer surface;

an inner surface; and a bar coupled to the frame and disposed above the outer surface, the bar and the frame forming an elongate slot between the bar and the outer surface of the frame, the slot disposed in a direction along a normal vector of the outer surface;

an extension portion extending away from a surface of a wrist of a patient when the device is positioned on the wrist, the extension portion having a convex surface facing the surface of the wrist of the patient;

an inflatable chamber disposed on the inner surface of the frame; and a wristband configured to secure the frame to a patient, wherein the wristband is configured to be inserted through the elongate slot and wrap around the bar;

wherein the extension portion is configured to engage the wristband when it is positioned around the bar, such that the extension portion causes a portion of the wristband to extend away from the surface of the wrist of the patient.

2. The device of claim 1, wherein the wristband is configured to secure the frame to a wrist of a patient such that the inflatable chamber is positioned adjacent to the radial artery.

3. The device of claim 1, wherein the frame further comprises a curved portion contoured to curve around a thumb-side portion of a wrist and a straight portion opposite the curved portion.

4. The device of claim 1, wherein the extension portion comprises:

a straight, angled segment; and a curved segment, wherein the straight, angled segment is disposed between the curved segment and the straight portion of the frame.

5. The device of claim 4, wherein the straight, angled segment comprises an angle ranging from zero degrees to 45 degrees relative to a plane extending from the straight portion, wherein the straight, angled segment comprises a length ranging up to 13 millimeters, and wherein the straight, angled segment is angled toward the bar.

6. The device of claim 4, wherein the curved segment comprises an outside radius up to 15 millimeters;

wherein the curved segment comprises a length ranging up to 13 millimeters, and wherein the curved segment is curved toward the bar.

7. The device of claim 1, wherein the extension portion comprises a flexible material.

8. The device of claim 1, wherein the wristband comprises a fastening system configured to couple a first portion of the wristband to a second portion of the wristband.

9. A frame for a radial artery compression device, comprising: a curved portion;

a straight portion opposite the curved portion;

an extension portion extending from the straight portion, the extension portion having a convex surface facing a surface of a wrist of a patient; and a bar oriented perpendicular to a longitudinal axis of the straight portion and coupled to and disposed above an outer surface of the straight portion in a direction away from the outer surface opposite the direction of an inner surface of the straight portion, the bar forming an elongate slot between the bar and the outer surface of the straight portion frame, wherein the bar is disposed between the extension portion and the straight portion;

wherein the extension portion angles away from the wrist of the patient when the device is positioned onto the wrist;

wherein the extension portion is configured to engage a wristband coupled to the bar, such that the extension portion causes a portion of the wristband to extend away from a surface of the wrist of the patient.

10. The frame of claim 9, wherein curved portion comprises a contour configured to curve around a thumb-side portion of a wrist.

11. The frame of claim 10, wherein the extension portion comprises:

a straight, angled segment; and a curved segment, wherein the straight, angled segment is disposed between curved segment and the straight portion of the frame.

12. The frame of claim 11, wherein the straight, angled segment comprises an angle ranging from zero degrees to 45 degrees relative to a plane extending from the straight portion, wherein the straight, angled segment comprises a length ranging up to 13 millimeters, and wherein the straight, angled segment is angled toward the bar.

13. The frame of claim 11, wherein the curved segment comprises an outside radius ranging up to 15 millimeters;

wherein the curved segment comprises a length ranging up to 13 millimeters, and wherein the curved segment is curved toward the bar.

14. The frame of claim 9, wherein the extension portion comprises a flexible material.

* * * * *